(12) United States Patent
Golde et al.

(10) Patent No.: US 7,786,283 B2
(45) Date of Patent: Aug. 31, 2010

(54) BRI CONSTRUCTS AND METHODS OF USING

(75) Inventors: Todd Eliot Golde, Ponte Vedra Beach, FL (US); Eileen M. McGowan, Jacksonville, FL (US); Pritam Das, Ponte Vedra Beach, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 602 days.

(21) Appl. No.: 10/185,297

(22) Filed: Jun. 28, 2002

(65) Prior Publication Data

US 2003/0221204 A1    Nov. 27, 2003

Related U.S. Application Data

(60) Provisional application No. 60/302,202, filed on Jun. 29, 2001.

(51) Int. Cl.
C07H 21/04    (2006.01)
C12N 15/00    (2006.01)

(52) U.S. Cl. .................................. 536/23.5; 435/320.1
(58) Field of Classification Search .............. 435/320.1; 536/23.1, 23.2, 23.4, 23.5
See application file for complete search history.

(56) References Cited

U.S. PATENT DOCUMENTS 5,877,399 A    3/1999    Hsiao et al.

OTHER PUBLICATIONS

GenBank Accession No. AA682331 (1997) EST sequence from human brain cDNA library.*
GenBank Accession No. AF272044 (Jul. 31, 2000) Mus musculus BRI3 mRNA, complete coding sequence.*
Stratagene Catalog (1994), pp. 304-305, pBluescript SK- vector map.*
Studier et al. (1990) Use of T7 RNA polymerase to direct expression of cloned genes. Methods in Enzymology 185: 60-89.*
GenBank Accession No. AF152462.
GenBank Accession No. AF246221.
GenBank Accession No. AF272043.
GenBank Accession No. AF272044.
Asami-Odaka et al., "Long Amyloid β-Protein Secreted from Wild-Type Human Neuroblastoma IMR-32 Cells," *Biochemistry*, 1995, 34:10272-10278.
Carlson et al., "Genetic modification of the phenotypes produced by amyloid precursor protein overexpressed in transgenic mice," *Human Molecular Genetics*, 1997, 6(11):1951-1959.
Chapman et al., "Impaired synaptic plasticity and learning in aged amyloid precursor protein transgenic mice," *Nature Neuroscience*, 1999, 2(3):271-276.
Duff et al., "Increased amyloid-β42(43) in brains of mice expressing mutant presenilin 1," *Nature*, 1996, 383:710-713.

Frenkel et al., "Generation of auto-antibodies towards Alzheimer's disease vaccination," *Vaccine*, 2001, 19:2615-2619.
Golde et al., "Biochemical detection of Aβ isoforms: implications for pathogenesis, diagnosis, and treatment of Alzheimer's disease," *Biochim. Biophys. Acta*, 2000, 1502:172-187.
Gómez-Isla et al., "Neuronal Loss Correlates with but Exceeds Neurofibrillary Tangles in Alzheimer's Disease," *Ann. Neurol.*, 1997, 41:17-24.
Holcomb et al., "Accelerated Alzheimer-type phenotype in transgenic mice carrying both mutant *amyloid precursor protein* and *presenilin 1* transgenes," *Nature Med.*, 1998, 4:97-100.
Hsiao, "Understanding the Biology of β-Amyloid Precursor Proteins in Transgenic Mice," *Neurobiol. Aging*, 1995, 16(4):705-706.
Hsiao et al., "Age-Related CNS Disorder and Early Death in Transgenic FVB/N Mice Overexpressing Alzheimer Amyloid Precursor Proteins," *Neuron*, 1995, 15:1203-1218.
Iadecola et al., "SOD1 rescues cerebral endothelial dysfunction in mice overexpressing amyloid precursor protein," *Nature Neuroscience*, 1999, 2(2):157-161.
Kim et al., "Furin mediates enhanced production of fibrillogenic ABri peptides in familial British dementia," *Nature Neuroscience*, 1999, 2(11):984-988.
Kumar, "Alzheimer's disease: amyloid β-peptide antibody vaccine as plaque remover," *J. Biosci.*, 2000, 25(4):315-316.
Lee et al., "Complete Genomic Sequence and Analysis of the Prion Protein Gene Region from Three Mammalian Species," *Genome Res.*, 1998, 8:1022-1037.
Lewis et al., "Specific Production of Aβ Peptides from Bri-Aβ Fusion Proteins," *Neurobiology of Aging*, 2000, vol. 21, Suppl. 1, Abstracts from the 7th International Conference on Alzheimer's Disease and Related Disorders, p. S199, Abstract No. 906.
Lewis et al., "Expression of BRI-amyloid β peptide fusion proteins: a novel method for specific high-level expression of amyloid β peptides," *Biochim. Biophys. Acta*, 2001, 1537:58-62.
Marwick, "Promising Vaccine Treatment for Alzheimer Disease Found," *JAMA*, 2000, 284(12):1503-1505.

(Continued)

*Primary Examiner*—Anne-Marie Falk
(74) *Attorney, Agent, or Firm*—Fish & Richardson P.C.

(57) ABSTRACT

The invention provides constructs that feature a nucleic acid molecule encoding an amino terminal region of a BRI polypeptide. A construct of the invention can further include a multiple cloning site joined to the 3' end of the BRI nucleic acid molecule or a nucleic acid molecule encoding a heterologous polypeptide operably linked to the BRI nucleic acid molecule. The invention further provides methods of directing a heterologous polypeptide through the secretory pathway in a cell. Such methods utilize a construct of the invention that additionally contains a promoter that directs expression of the BRI and heterologous nucleic acid molecules. The construct is introduced into a cell and, following expression, the fusion protein is directed through the secretory pathway of the cell. In addition, a construct of the invention can be introduced into an animal to make the animal transgenic for the heterologous polypeptide.

25 Claims, 6 Drawing Sheets

OTHER PUBLICATIONS

Morgan et al., "Aβ peptide vaccination prevents memory loss in an animal model of Alzheimer's disease," *Nature*, 2000, 408:982-985.

Mullan et al., "A pathogenic mutation for probable Alzheimer's disease in the APP gene at the N-terminus of β-amyloid," *Nature Genetics*, 1992, 1:345-347.

Murphy et al., "γ-Secretase, Evidence for Multiple Proteolytic Activities and Influence of Membrane Positioning of Substrate on Generation of Amyloid β Peptides of Varying Length," *J. Biol. Chem.*, 1999, 274(17):11914-11923.

Snyder et al., "Multipotent Neural Cell Lines Can Engraft and Participate in Development of Mouse Cerebellum," *Cell*, 1992, 68:33-51.

Sturchler-Pierrat et al., "Two amyloid precursor protein transgenic mouse models with Alzheimer disease-like pathology," *Proc. Natl. Acad. Sci. USA*, 1997, 94:13287-13292.

Suzuki et al., "An Increased Percentage of Long Amyloid β Protein Secreted by Familial Amyloid β Protein Precursor ($\beta APP_{717}$) Mutants," *Science*, 1994, 264:1336-1340.

Vidal et al., "Sequence, genomic structure and tissue expression of Human $BRI_3$, a member of the BRI gene family," *Gene*, 2001, 266:95-102.

Younkin, "Amyloid β vaccination: reduced plaques and improved cognition," *Nature Medicine*, 2001, 7:18-19.

Zhang et al., "Increased Susceptibility to Ischemic Brain Damage in Transgenic Mice Overexpressing the Amyloid Precursor Protein," *J. Neuroscience*, 1997, 17(20):7655-7661.

El-Agnaf et al., "Effect of the Disulfide Bridge and the C-Terminal Extension on the Oligomerization of the Amyloid Peptide ABri Implicated in Familial British Dementia," *Biochemistry*, 2001, 40:3449-3457.

El-Agnaf et al., "Non-fibrillar Oligomeric Species of the Amyloid ABri Peptide, Implicated in Familial British Dementia, are more Potent at Inducing Apoptotic Cell Death than Protofibrils or Mature Fibrils," *J. Mol. Biol.*, 2001, 310:157-168.

Pickford et al., "Modelling Familial British Dementia in transgenic mice," *Society for Neuroscience Abstracts*, 2001, 27(2):2342, Abstract.

Rostagno et al., "Complement activation in Bri dementias and Alzheimer's disease," *Society for Neuroscience Abstracts*, 2001, 27(2)2562, Abstract.

Schwab et al., "Familial British dementia: A brain amyloidosis associated with Alzheimer-like neurofibrillary tangles," *Society for Neuroscience Abstracts*, 2001, 27(2):1997, Abstract.

Vidal et al., "A stop-codon mutation in the *BRI* gene associated with familial British dementia," *Nature*, 1999, 399:776-781.

Vidal et al., "Sequence, genomic structure and tissue expression of Human $BRI_3$, a member of the BRI gene family," *Gene*, 2001, 266:95-102.

\* cited by examiner

```
atggtgaaggtgacgttcaactccgctctggcccagaaggaggccaagaaggacgagcccaagagcggc
 M  V  K  V  T  F  N  S  A  L  A  Q  K  E  A  K  K  D  E  P  K  S  G gaggaggcgctcatcatcccccccgacgccgtcgcggtggactgcaaggacccagatgatgtggtacca
 E  E  A  L  I  I  P  P  D  A  V  A  V  D  C  K  D  P  D  D  V  V  P gttggccaaagaagagcctggtgttggtgcatgtgctttggactagcatttatgcttgcaggtgttatt
 V  G  Q  R  R  A  W  C  W  C  M  C  F  G  L  A  F  M  L  A  G  V  I ctaggaggagcatacttgtacaaatattttgcacttcaaccagatgacgtgtactactgtggaataaag
 L  G  G  A  Y  L  Y  K  Y  F  A  L  Q  P  D  D  V  Y  Y  C  G  I  K tacatcaaagatgatgtcatcttaaatgagccctctgcagatgccccagctgctctctaccagacaatt
 Y  I  K  D  D  V  I  L  N  E  P  S  A  D  A  P  A  A  L  Y  Q  T  I gaagaaaatattaaaatctttgaagaagaagaagttgaattatcagtgtgcctgtcccagagtttgca
 E  E  N  I  K  I  F  E  E  E  E  V  E  F  I  S  V  P  V  P  E  F  A gatagtgatcctgccaacattgttcatgactttaacaagaaacttacagcctatttagatcttaacctg
 D  S  D  P  A  N  I  V  H  D  F  N  K  K  L  T  A  Y  L  D  L  N  L gataagtgctatgtgatccctctgaacacttccattgttatgccacccagaaacctactggagttactt
 D  K  C  Y  V  I  P  L  N  T  S  I  V  M  P  P  R  N  L  L  E  L  L attaacatcaaggctggaacctatttgcctcagtcctatctgattcatgagcacatggttattactgat
 I  N  I  K  A  G  T  Y  L  P  Q  S  Y  L  I  H  E  H  M  V  I  T  D cgcattgaaaacattgatcacctgggtttctttatttatcgactgtgtcatgacaaggaaacttacaaa
 R  I  E  N  I  D  H  L  G  F  F  I  Y  R  L  C  H  D  K  E  T  Y  K ctgcaacgcagagaaactattaaaggtattcagaaacgtgatgcagaattccgacatgactcaggatat
 L  Q  R  R  E  T  I  K  G  I  Q  K  R  D  A  E  F  R  H  D  S  G  Y gaagttcatcatcaaaaattggtgttctttgcagaagatgtgggttcaaacaaaggtgcaatcattgga
 E  V  H  H  Q  K  L  V  F  F  A  E  D  V  G  S  N  K  G  A  I  I  G ctcatggtgggcggtgttgtctag
 L  M  V  G  G  V  V  *
```

Figure 2

```
atggtgaaggtgacgttcaactccgctctggcccagaaggaggccaagaaggacgagcccaagagcggc
 M  V  K  V  T  F  N  S  A  L  A  Q  K  E  A  K  K  D  E  P  K  S  G gaggaggcgctcatcatccccccgacgccgtcgcggtggactgcaaggacccagatgatgtggtacca
 E  E  A  L  I  I  P  P  D  A  V  A  V  D  C  K  D  P  D  D  V  V  P gttggccaagaagagcctggtgttggtgcatgtgctttggactagcatttatgcttgcaggtgttatt
 V  G  Q  R  R  A  W  C  W  C  M  C  F  G  L  A  F  M  L  A  G  V  I ctaggaggagcatacttgtacaaatattttgcacttcaaccagatgacgtgtactactgtggaataaag
 L  G  G  A  Y  L  Y  K  Y  F  A  L  Q  P  D  D  V  Y  Y  C  G  I  K tacatcaaagatgatgtcatcttaaatgagccctctgcagatgccccagctgctctctaccagacaatt
 Y  I  K  D  D  V  I  L  N  E  P  S  A  D  A  P  A  A  L  Y  Q  T  I gaagaaaatattaaaatctttgaagaagaagaagttgaatttatcagtgtgcctgtcccagagtttgca
 E  E  N  I  K  I  F  E  E  E  E  V  E  F  I  S  V  P  V  P  E  F  A gatagtgatcctgccaacattgttcatgactttaacaagaaacttacagcctatttagatcttaacctg
 D  S  D  P  A  N  I  V  H  D  F  N  K  K  L  T  A  Y  L  D  L  N  L gataagtgctatgtgatccctctgaacacttccattgttatgccacccagaaacctactggagttactt
 D  K  C  Y  V  I  P  L  N  T  S  I  V  M  P  P  R  N  L  L  E  L  L attaacatcaaggctggaacctatttgcctcagtcctatctgattcatgagcacatggttattactgat
 I  N  I  K  A  G  T  Y  L  P  Q  S  Y  L  I  H  E  H  M  V  I  T  D cgcattgaaaacattgatcacctgggtttctttatttatcgactgtgtcatgacaaggaaacttacaaa
 R  I  E  N  I  D  H  L  G  F  F  I  Y  R  L  C  H  D  K  E  T  Y  K ctgcaacgcagagaaactattaaaggtattcagaaacgtgatgcagaattccgacatgactcaggatat
 L  Q  R  R  E  T  I  K  G  I  Q  K  R  D  A  E  F  R  H  D  S  G  Y gaagttcatcatcaaaaattggtgttctttgcagaagatgtgggttcaaacaaaggtgcaatcattgga
 E  V  H  H  Q  K  L  V  F  F  A  E  D  V  G  S  N  K  G  A  I  I  G ctcatggtgggcggtgttgtcatagcgtag
 L  M  V  G  G  V  V  I  A  *
```

BRI CONSTRUCTS AND METHODS OF USING

CROSS REFERENCE TO RELATED APPLICATIONS

This application claims priority under 35 U.S.C. §119(e) of U.S. provisional application Ser. No. 60/302,202, filed Jun. 29, 2001.

TECHNICAL FIELD

This invention relates to nucleic acid constructs that can be used to direct polypeptides through the secretory pathway of a cell.

BACKGROUND

A variety of quality control mechanisms operate in the secretory pathway to ensure the fidelity and regulation of protein expression during cell life and differentiation. As a rule, only proteins that pass a stringent quality control process are transported to their target organelles and compartments. If proper maturation fails, the aberrant products are degraded. Quality control improves folding efficiency by retaining proteins in the environment of the endoplasmic reticulum until proper folding, and prevents harmful effects caused by the release of incompletely folded or assembled proteins. The secretory pathway, therefore, can be used to assist in proper folding and assembly of a heterologous polypeptide.

SUMMARY

The invention provides BRI constructs and methods of using such constructs for directing a heterologous polypeptide through the secretory pathway. Movement through the secretory pathway ensures proper folding and post-translational modification of the heterologous polypeptide. The constructs of the invention can be used to generate a BRI-heterologous polypeptide fusion protein, which can be directed through the secretory pathway and cleaved so as to release the heterologous polypeptide. Cleavage of the fusion protein to release the heterologous polypeptide can occur within the Golgi apparatus or at the membrane if the BRI portion of the fusion protein is deposited appropriately. Heterologous polypeptides suitable for use in the invention include, for example, therapeutic or diagnostic polypeptides.

In one aspect, the invention provides constructs having a first nucleic acid molecule joined at its 3' end to nucleotides that include a multiple cloning site. In such a construct, the first nucleic acid molecule encodes an amino terminal region of a BRI polypeptide.

In another aspect, the invention provides constructs having a first nucleic acid molecule operably linked at its 3' end to a second nucleic acid molecule. In such a construct, the first nucleic acid molecule encodes an amino terminal region of a BRI polypeptide, and the second nucleic acid molecule encodes a heterologous polypeptide. The heterologous polypeptide can be, for example, a β-amyloid polypeptide. The β-amyloid polypeptide can be a wild-type β-amyloid polypeptide, a naturally occurring mutant of a β-amyloid polypeptide, a truncated amyloid β-polypeptide, or a β amyloid polypeptide containing substitutions at one or more residues. In addition, a β-amyloid polypeptide can be a mammalian β-amyloid polypeptide such as a human, a mouse, a guinea pig, and a rat β-amyloid polypeptide.

The amino terminal region of the BRI polypeptide consists essentially of 243 amino terminal residues of a BRI polypeptide. An operable linkage typically includes nucleotides encoding a dibasic cleavage site, such as a Lysine-Arginine.

Constructs of the invention can further include a promoter operably linked to the 5' end of the first nucleic acid molecule. Such a promoter can be a prion promoter, for example, a mouse prion promoter. Alternatively, such a promote can be a β-actin promoter, for example, a chicken β-actin promoter. BRI polypeptides of the invention can be a human BRI polypeptide or a mouse BRI polypeptide.

In another aspect, the invention provides an isolated nucleic acid molecule consisting essentially of nucleotides encoding an amino terminal region of a BRI polypeptide and an isolated polypeptide consisting essentially of an amino terminal region of a BRI polypeptide. In yet another aspect, the invention provides a fusion polypeptide including an amino terminal region of a BRI polypeptide operably linked to a heterologous polypeptide.

In still another aspect of the invention, there is provided methods of directing a heterologous polypeptide through the secretory pathway of a cell. Such methods include introducing a construct of the invention into a cell, wherein expression of the construct in the cell results in a BRI-heterologous polypeptide fusion protein that is directed through the secretory pathway of the cell. A heterologous polypeptide can be, for example, a therapeutic polypeptide. Representative therapeutic polypeptides include a β-amyloid polypeptide or a polypeptide having binding affinity for a β-amyloid polypeptide, and can further include a growth factor, a cytokine, a hormone, and an antigen such as a bacterial antigen, a viral antigen, or a neoplastic antigen.

Methods to deliver a heterologous polypeptide to a cell can include cells in vivo (e.g., an animal such as a mouse, a rat, a guinea pig, and a human). Generally, an animal can be administered the construct intraperitoneally, intramuscularly, intranasally or transdermally. Oftentimes, expression of the BRI-heterologous polypeptide fusion protein in the animal elicits an immune response in the animal to the heterologous polypeptide. In such cases in which it is desirable to elicit an immune response, constructs of the invention can further contain a third nucleic acid molecule encoding an immunogenic tag operably linked to the second nucleic acid molecule. Further, following movement of the BRI-heterologous polypeptide fusion protein through the secretory pathway of a cell, the BRI-heterologous polypeptide fusion protein can be cleaved. In an embodiment of the invention, cleavage of the BRI-heterologous polypeptide fusion protein delivers the heterologous polypeptide to the vascular system of the animal.

In another aspect of the invention, there is provided a transgenic animal whose genome comprises a construct of the invention. Generally, expression of the construct results in detectable levels of a BRI-heterologous polypeptide fusion protein in the animal. Representative animals useful in the invention include mice, rats, and guinea pigs. In a transgenic animal containing a construct of the invention that includes a β-amyloid polypeptide can exhibit impaired performance in memory and learning tests, and abnormal neuropathology in a cortico-limbic region of the animal's brain compared to a control animal lacking the construct. Such abnormal neuropathology can include the presence of immunoreactive β-amyloid deposits; an elevated number of thioflavin S-positive β-amyloid deposits; an increased amount of thioflavin S-positive β-amyloid deposits; hypertrophic gliosis in the cortico-limbic structures of the brain; diminution of 2-deoxyglucose uptake in the cortico-limbic structures of the brain; and diminution of 2-deoxyglucose utilization in the cortico-limbic structures of the brain.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

FIG. 1A shows an IP/MS analysis of conditioned media from a stable H4 cell line expressing pAG3BRI-Aβ1-40. Aβ species are indicated above the peaks and the mass of each is enclosed in parentheses. FIG. 1B is an IP/MS analysis of conditioned media from a stable H4 cell line expressing BRI-Aβ1-42.

FIG. 2 is the nucleotide and amino acid sequence of the BRI-Aβ1-40 (SEQ ID NOs:1 and 2, respectively) portion of pAG3BRI-Aβ1-40. The Aβ1-40 sequence is shown in bold.

FIG. 3 is the nucleotide and amino acid sequence of BRI-Aβ1-42 (SEQ ID NOs:3 and 4, respectively) portion of pAG3BRI-Aβ1-42. The Aβ1-42 sequence is shown in bold.

Like reference symbols in the various drawings indicate like elements.

DETAILED DESCRIPTION

Figure 1:
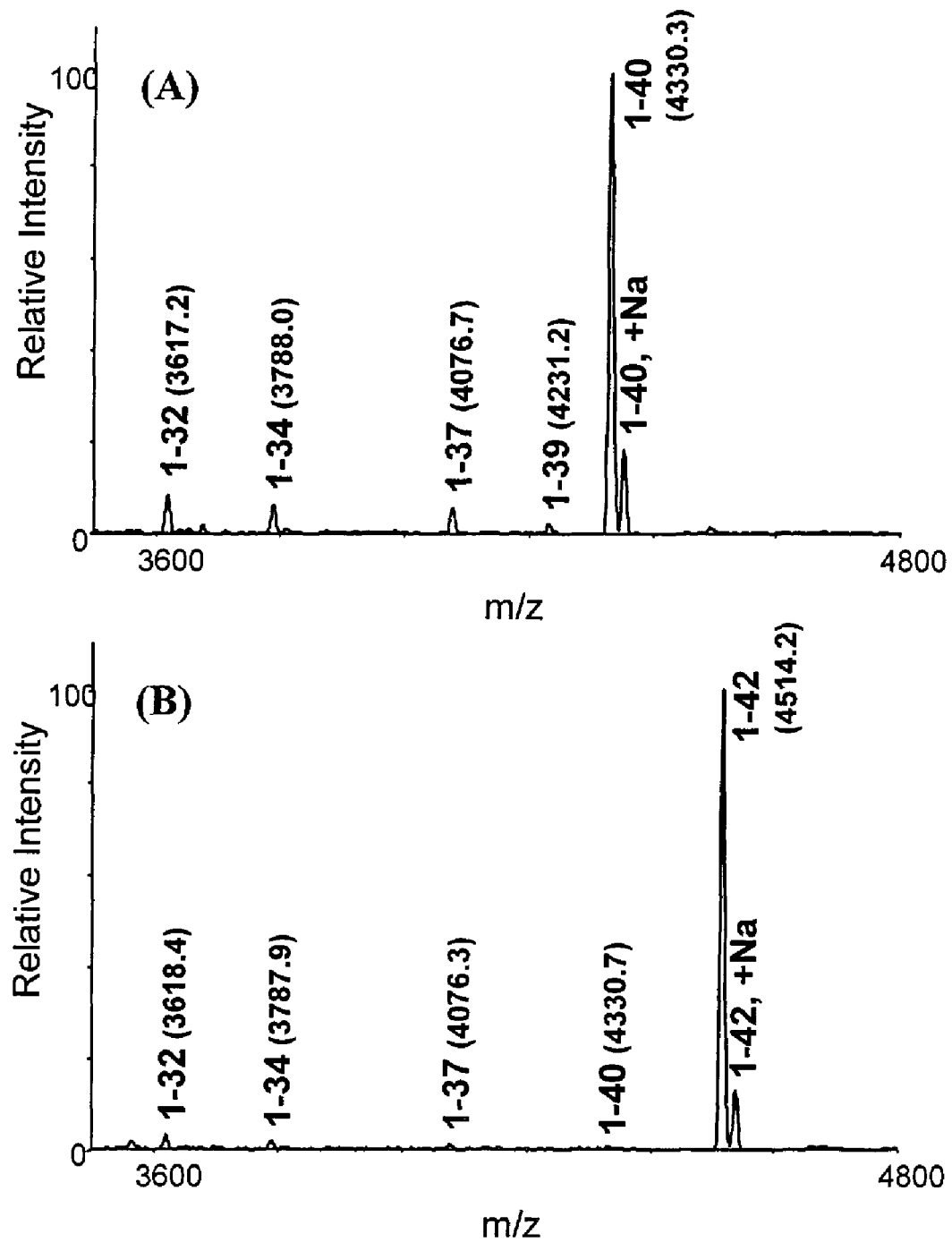
FIG. 1 is an analysis of BRI-Aβ fusion proteins.

The invention provides BRI constructs and methods of using such constructs for directing a heterologous polypeptide through the secretory pathway. BRI constructs of the invention feature a nucleic acid molecule encoding an amino terminal region of a BRI polypeptide. Movement through the secretory pathway ensures proper folding and post-translational modification of the heterologous polypeptide. Constructs of the invention can be used to generate a BRI-heterologous polypeptide fusion protein, which can be directed through the secretory pathway and cleaved so as to release the heterologous polypeptide. Cleavage of the fusion protein to release the heterologous polypeptide can occur within the Golgi apparatus or at the membrane if the BRI portion of the fusion protein is deposited appropriately. Heterologous polypeptides suitable for use in the invention include, for example, therapeutic or diagnostic polypeptides. In addition, a construct of the invention can be introduced into an animal to produce an animal that is transgenic for the heterologous polypeptide.

Origin of BRI

Familial British dementia (FBD) is an autosomal dominant form of cerebral amyloid angiopathy (CAA) clinically characterized by progressive dementia, spastic tetraparesis and cerebellar ataxia, with an age of onset in the fourth to fifth decade and full penetrance by age 60. Many areas of the central nervous system are affected and neuropathological symptoms consist of (i) severe and widespread amyloid angiopathy of the brain and spinal cord with perivascular amyloid plaque formation, (ii) periventricular white matter changes resembling Binswanger's leukoencephalopathy, (iii) nonneuritic amyloid plaques affecting the cerebellum, hippocampus, amygdala and, occasionally, the cerebral cortex, and (iv) neurofibrillary degeneration of hippocampal neurons. Large intracerebral hemorrhage is a rare feature of the disease. Because of the extensive cerebrovascular involvement, the disorder previously has been designated as familial cerebral amyloid angiopathy-British type and cerebrovascular amyloidosis-British type.

Amyloid fibrils in FBD include a 4 kDa insoluble protein named ABri. This protein is the abnormal product of a gene on chromosome 13 designated BRI. The wild-type BRI polypeptide is 266 amino acid residues with a calculated $M_r$ of 30,329. In FBD, there is a single nucleotide substitution in the stop codon (TGA to AGA at codon 267) resulting in the presence of an arginine residue and an open reading frame of 277 residues. Following cleavage of the wild-type protein, a 23 amino acid residue C-terminal fragment is produced, while cleavage of the mutant BRI protein generates a 34 amino acid fragment that forms the pathogenic amyloid plaques. The function of the wild-type BRI protein or the wild-type 22 residue C-terminal fragment remains unknown. Hydropathy analysis indicates the presence of a putative single transmembrane spanning domain from residues 52 to 74, suggesting that BRI is a type II integral transmembrane protein with the C-terminal part being extracellular. A putative single N-glycosylation site is located at asparagine 170.

A second neurodegenerative disease is associated with the BRI gene. This disease was identified in a Danish family, and was named familial Danish dementia (FDD). FDD is an autosomal dominant disorder characterized by cataracts, deafness, progressive ataxia and dementia. Neuropathological findings are similar to the neuropathology observed in FBD. The cloning and sequencing of the BRI gene from patients with FDD revealed the presence of a ten-nucleotide duplication (795-796insTTTAATTTGT (SEQ ID NO:12)) between codons 265 and 266, just before the normal stop-codon at residue 267. The decamer duplication mutation produces a frame-shift in the BRI sequence generating a mutant BRI protein of 277 amino acids of which the amyloid (ADan) comprises the last 34 C-terminal amino acids.

A dibasic consensus sequence (KR↓ or RR↓) for proprotein convertases (PCs) belonging to the subtilisin superfamily of calcium-dependent serine endoproteases is located immediately before the ABri and ADan N-terminal sequences. The consensus sequence for PCs exists in all three BRI isoforms, including the mouse BRI homologue and the *Caenorhabditis briggsae* BRI-LP. PCs act within the secretory pathway to cleave polypeptide precursors, thereby generating their active forms.

Of the seven PCs identified in human, the best known is furin, a ubiquitous endopeptidase of the constitutive secretory pathway. Human and mouse $BRI_2$ and $BRI_3$ and the *C. briggsae* BRI-LP have the putative recognition sequence for furin. The $BRI_1$ isoform, however, does not, perhaps precluding the cleavage of $BRI_1$ by furin. It has been reported that wild-type $BRI_2$ and the British mutant form of $BRI_2$ both can be cleaved by furin, although other members of the PC family may also be able to process $BRI_2$. The different PCs may play a pivotal role in processing the BRI family of polypeptides and, hence, in the generation of the amyloid peptides from the mutant BRIs thereby resulting in FBD and FDD. Furin and other PCs also may have a functional role in tumor cell invasion and progression.

BRI Nucleic Acids and Polypeptides

The BRI gene family is made up of at least three different genes ($BRI_1$, $BRI_2$, and $BRI_3$). The cDNA sequences of the human and mouse $BRI_1$ and $BRI_2$ genes have been determined, as has the complete cDNA sequence of the human $BRI_3$ gene. The amino acid sequence of human $BRI_3$ is 43.7% identical to the amino acid sequence of human $BRI_2$, and 38.3% identical to that of human $BRI_1$, with the highest percentage of amino acid identity being concentrated on the C-terminal half of the molecule. Similarly, the mouse and rat amino acid sequences are 95.5% and 96.2% identical, respectively, to the human $BRI_1$ homologue, whereas the chicken sequence exhibits 75.9% homology to the human $BRI_1$. The nucleotide sequence of the human BRI transcript is highly homologous to EST clones from chicken, rat, mouse, rabbit, and pig origin, and to a sequence from *C. briggsae*, indicating that the BRI gene belongs to a conserved gene family.

The invention provides isolated nucleic acid molecules consisting essentially of nucleotides encoding an amino terminal region of a BRI polypeptide. BRI nucleic acid molecules can be DNA or RNA, linear or circular, an din sense or antisense orientation. BRI nucleic acids consisting essentially of nucleotides encoding an amino terminal region of a BRI polypeptide refers to nucleic acid sequences that encode at least a BRI transmembrane spanning domain, including signal sequences required to get the polypeptide to the membrane, and an appropriate PC cleavage sequence. BRI nucleic acids consisting essentially of nucleotides encoding an amino terminal region of a BRI polypeptide are, however, nucleic acids that encode less than a full length BRI polypeptide. A BRI nucleic acid molecule of the invention includes, for example, nucleic acid sequences encoding a BRI polypeptide up to and including the cleavage sequence (e.g., 243 amino terminal residues of $BRI_2$). The invention also provides polypeptides consisting essentially of an amino terminal region of a BRI polypeptide. Similarly, a polypeptide consisting essentially of an amino terminal region of a BRI polypeptide includes at least the functional domains described above and can include the entire amino terminal region up to and including the cleavage sequence (e.g., 243 amino terminal residues from $BRI_2$). Representative human BRI nucleic acid sequences and the encoded polypeptides are described in GenBank Accession Nos. AF272043, AF246221, and AF152462. By way of example, amino terminal regions of such BRI polypeptides include residues 1-242, 1-243 and 1-243, respectively. A mouse BRI nucleic acid sequence and the encoded polypeptide are described in GenBank Accession No. AF272044 and an example of an amino terminal region of a mouse BRI polypeptide is residues 1-244. The sequence of an amino terminal region of a BRI polypeptide also can be used to design a corresponding BRI nucleic acid.

BRI polypeptides from which amino terminal regions are derived include known BRI polypeptides (e.g., $BRI_1$, $BRI_2$, and $BRI_3$). An amino terminal region of a BRI polypeptide suitable for use in the invention has at least about 75% sequence identity, for example, at least about 80% 90%, or 95% sequence identity to the amino terminal region of a known BRI polypeptide. According to the invention, percent sequence identity is determined for any subject nucleic acid or amino acid sequence relative to a known BRI nucleic acid or BRI amino acid sequence as follows. First, a known BRI nucleic acid or BRI amino acid sequence is compared and aligned to a subject nucleic acid or amino acid sequence using the BLAST 2 Sequences (Bl2seq) program from the stand-alone version of BLASTZ (e.g., version 2.0.14). The stand-alone version of BLASTZ can be obtained at ncbi.nlm.nih.gov on the World Wide Web. The algorithms also are described in detail by Karlin et al. (*Proc. Natl. Acad. Sci. USA*, 87:2264 (1990) and 90:5873 (1993)) and Altschul et al. (*Nucl. Acids Res.*, 25:3389 (1997)). Bl2seq can perform a comparison between the subject sequence and a known BRI sequence using either the BLASTN (to compare nucleic acid sequences) or BLASTP (to compare amino acid sequences) algorithm. If necessary, gaps of one or more residues are inserted into the known BRI or the subject sequence to maximize sequence alignments between structurally conserved domains (e.g., α-helices, β-sheets, and loops). Default parameters are used when performing sequence alignments according to the invention. Once aligned, a length is determined by counting the number of nucleotides or amino acid residues from the known BRI sequence that match the subject sequence starting with any matched position and ending with any other matched position. A matched position is any position where an identical nucleotide or amino acid residue is present in both the known BRI sequence and the subject sequence.

The percent identity over a particular length is determined by counting the number of matched positions over that particular length, dividing that number by the length and multiplying the resulting value by 100. For example, if (i) a 1000 nucleotide known BRI sequence is compared to a subject nucleic acid sequence (e.g., a putative BRI sequence), (ii) the Bl2seq program presents 200 nucleotides from the known BRI sequence aligned with a region of the subject sequence where the first and last nucleotides of that 200 nucleotide region are matches, and (iii) the number of matches over those 200 aligned nucleotides is 180, then the 1000 nucleotide known BRI sequence possesses a sequence identity with the subject sequence of 90% over 200 nucleotides (i.e., 180÷200×100=90). It will be appreciated that a known BRI nucleic acid or amino acid sequence that aligns with a subject sequence can result in many different lengths with each length having its own percent identity. It is noted that the percent identity value can be rounded to the nearest tenth. For example, 78.11, 78.12, 78.13, and 78.14 is rounded down to 78.1, while 78.15, 78.16, 78.17, 78.18, and 78.19 is rounded up to 78.2. It is also noted that the length value will always be an integer.

As used herein, "isolated" refers to a nucleic acid molecule corresponding to part or all of a gene encoding a BRI polypeptide, but free of sequences that normally flank one or both sides of the wild-type gene in a naturally occurring genome. The term "isolated" as used herein with respect to nucleic acids also includes any non-naturally-occurring nucleic acid sequence. An isolated nucleic acid includes, for example, a DNA molecule, provided one of the nucleic acid sequences normally found immediately flanking that DNA molecule in a naturally-occurring genome is removed or absent. Thus, an isolated BRI nucleic acid molecule includes, without limitation, a BRI DNA molecule that exists as a separate molecule (e.g., a cDNA or genomic DNA fragment produced by PCR or restriction endonuclease digestion) independent of other sequences, as well as BRI DNA that is incorporated into a vector, an autonomously replicating plasmid, or a virus (e.g., a retrovirus, adenovirus, or herpes virus). In addition, an isolated nucleic acid can include a recombinant BRI DNA molecule that is part of a hybrid or fusion nucleic acid molecule. A nucleic acid molecule existing among hundreds to millions of other nucleic acid molecules within, for example, a nucleic acid library (e.g., a cDNA, or genomic library) or a portion of a gel (e.g., agarose, or polyacrylamine) containing restriction-digested genomic DNA is not to be considered an isolated nucleic acid.

An isolated BRI nucleic acid molecule of the invention includes fragments of at least about 20 nucleotides in length. For example, a fragment can be about 20, 30, 40, 50, 75, 100, or greater than 100 nucleotides in length, e.g., 150, 200, 300, 400, 500, or 1000 nucleotides in length. Such fragments, whether protein-encoding or not, can be used as probes, primers, and diagnostic reagents. Likewise, the invention provides for fragments of BRI polypeptides. Polypeptide fragments can include, for example, one or more functional domains or an antigenic epitope.

Isolated nucleic acid molecules within the scope of the invention can be obtained using any method including, without limitation, routine molecular cloning and chemical nucleic acid synthesis techniques. Polymerase chain reaction (PCR) techniques can be used to isolate a BRI nucleic acid molecule having a sequence that shares identity with art known BRI sequences. General PCR techniques are described, for example in *PCR Primer: A Laboratory Manual*, Dieffenbach & Dveksler, Eds., Cold Spring Harbor Laboratory Press, 1995. Furthermore, nucleic acid hybridization techniques can be used to isolate a nucleic acid within the scope of the invention. Briefly, a nucleic acid sequence encoding a BRI polypeptide can be used as a probe to identify a similar nucleic acid by hybridization under conditions of moderate to high stringency. Moderately stringent hybridization conditions include hybridization at about 42° C. in a hybridization solution containing 25 mM $KPO_4$ (pH 7.4), 5×SSC, 5× Denhart's solution, 50 μg/ml denatured, sonicated salmon sperm DNA, 50% formamide, 10% Dextran sulfate, and 1-15 ng/ml probe (about $5 \times 10^7$ cpm/μg), and wash steps at about 50° C. with a wash solution containing 2×SSC and 0.1% SDS. For high stringency, the same hybridization conditions can be used, but washes are performed at about 65° C. with a wash solution containing 0.2×SSC and 0.1% SDS. See, for example, sections 7.39-7.52 of Sambrook, Fritsch & Maniatis, *Molecular Cloning: A Laboratory Manual*, 2nd Ed., 1989, Cold Spring Harbor Laboratory Press, Plainview, N.Y. Once a nucleic acid is isolated, the nucleic acid then can be sequenced and analyzed to determine whether it is within the scope of the invention as described herein.

By an "isolated polypeptide" is meant a polypeptide that has been separated from at least some of those components that naturally accompany it. A polypeptide is isolated when it is at least 50%, by weight, free from the polypeptides and other naturally occurring organic molecules with which it is naturally associated in vivo. For example, a polypeptide is isolated if it is at least 60%, 70%, 75%, 80%, 85%, 90%, or 99%, by weight, free from other polypeptides. An isolated BRI polypeptide can be obtained, for example, by extraction from a natural source; by in vitro or in vivo expression of a recombinant BRI nucleic acid; or by chemically synthesizing a BRI polypeptide. BRI polypeptides also can be isolated using, e.g., immunoaffinity chromatography and an antibody specific for BRI, polyacrylamide gel electrophoresis, or HPLC analysis.

Heterologous Nucleic Acids and Polypeptides

As used herein, heterologous polypeptides refer to non-BRI polypeptides. A nucleic acid encoding a heterologous polypeptide suitable for use in the present invention can be one that encodes a therapeutic polypeptide, although the invention is not limited to any specific type of heterologous polypeptide. Alternatively, the heterologous polypeptide can be any polypeptide for purposes of experimental studies.

Nucleic acid molecules encoding heterologous therapeutic polypeptides are numerous, and the invention is not limited by the following examples. Representative therapeutic polypeptides include ion channel proteins such as CFTR; blood proteins such as Factor X; vasoconstrictors/vasodilators; bronchoconstrictors/bronchodilators; antibiotics; receptor ligand or receptor antagonists; enzymes or proenzymes; growth factors such as insulin-like growth factor or platelet-derived growth factor or growth factor antagonists; and cytokines such as IL-4, IL-18 or IFN-γ.

A toxin also can be used as a heterologous polypeptide in a construct and in methods of the invention. Toxins include plant and bacterial toxins such as abrin, diphtheria toxin, exotoxin, gelonin, and ricin. In addition, antigens are useful as heterologous polypeptides. Antigens can be, for example, bacterial antigens, viral antigens, or neoplastic antigens. A representative bacterial antigen is Ag85 from *Mycobacterium tuberculosis*; representative viral antigens include hepatitis B surface antigens, glycoprotein D from herpes simplex virus or pseudorabies virus, gag from HIV, or nucleocapsid proteins of a number of viruses; representative neoplastic antigens include human prostate specific antigen, E7 gene products, melanoma antigens gp100 and TRP02, Her2/neu, tumor-associated antigen, and carcinoembryonic antigen (CEA). By way of example, antigens can be used therapeutically, for example to inhibit e.g., a pathogen or, alternatively, as vaccines. Further, hormones such as steroids, progesterone or estrogen, or hormone antagonists can be particularly useful in constructs of the invention as certain cell types may retain hormones in the secretory pathway as a means of regulating hormonal release.

Alternatively, the heterologous polypeptide in a construct of the invention can be an Aβ polypeptide. To generate Aβ in vivo, amyloid precursor protein (APP) is sequentially cleaved by β-secretase and γ-secretase. β-secretase cleaves at the amino terminus of the Aβ sequence, producing a secreted derivative, sAPPβ, and the Aβ-bearing C-terminal fragment of 99 residues, CTFβ. CTFβ is subsequently cleaved by γ-secretase to release Aβ. An alternative cleavage activity, α-secretase, cleaves APP within Aβ (between residues 16 and 17) to generate the larger secreted derivative, sAPPα, and the membrane associated 83-residue fragment, CTFα. γ-secretase cleavage of CTFα generates P3. In addition, γ-secretase cleavage of either CTFα or CTFβ yields a C-terminal fragment of 57-59 residues, designated CTFγ. Biochemical and immunocytochemical studies have revealed that the Aβ polypeptides deposited in brains from patients with AD have substantial amino- and carboxyl-terminal heterogeneity and can contain from 39 to 43 amino acid residues, with Aβ1-40 and Aβ1-42 being the most predominant.

As used herein, an Aβ polypeptide corresponds to a portion of an APP (e.g., human APP) that is produced following cleavage by β-secretase and γ-secretase (for example, residues 671-711 (Aβ1-40) or 671-713 (Aβ1-42) of GenBank Accession No. D87675) or fragments thereof. An Aβ polypeptide useful in the invention can be a wild-type Aβ polypeptide, a naturally occurring mutant of an Aβ polypeptide, a truncated Aβ-polypeptide, or an Aβ polypeptide genetically engineered to contain substitutions at one or more residues. Such an Aβ polypeptide is preferably a mammalian Aβ polypeptide such as a human, mouse, guinea pig, or rat Aβ polypeptide, and can be obtained by methods routine in the art (e.g., PCR or chemical synthesis as described above).

BRI-Heterologous Polypeptide Fusion Constructs

The invention provides constructs having a first nucleic acid molecule encoding an amino terminal region of a BRI polypeptide joined at its 3' end to nucleotide sequences that include a multiple cloning site. As used herein, a "multiple cloning site," also known as a polylinker, refers to nucleic acid sequences containing at least one, and usually several, consensus sites for different restriction enzymes. It is understood that those of skill in the art will appreciate the various features that multiple cloning sites can offer such as the position of such sequences relative to a reading frame. The multiple cloning site sequences can be adjacent or proximal to the BRI nucleic acid molecule. It can be appreciated by those of skill in the art that proximal positioning of the BRI molecule and the multiple cloning site refers to a joining sequences encoding a few to several amino acid residues such that the BRI polypeptide, the heterologous polypeptide, or the cleavage site are not disrupted by the adjoining sequences. As used herein, the term "restriction enzymes" typically refers to endonuclease enzymes that cut double-stranded DNA at or near a specific consensus sequence. Constructs of the invention can further include a second nucleic acid molecule encoding a heterologous polypeptide operably linked to the 3' end of the first nucleic acid molecule encoding the amino-terminal region of BRI. Such a linkage produces a BRI-heterologous polypeptide fusion protein having an amino terminal region from a BRI polypeptide operably linked at its carboxy terminal region to the heterologous polypeptide.

Constructs, including expression constructs, suitable for use in the present invention are commercially available and/or produced by recombinant DNA technology methods routine in the art. A construct containing a BRI nucleic acid molecule additionally can have elements necessary for expression operably linked to such a BRI nucleic acid molecule, and further can include sequences such as those encoding a selectable marker (e.g., an antibiotic resistance gene), and/or those that can be used in purification of a BRI polypeptide or BRI-heterologous polypeptide fusion protein (e.g., 6×His tag). Elements necessary for expression include nucleic acid sequences that direct and regulate expression of BRI coding sequences and heterologous nucleic acid coding sequences, if present. Elements necessary for expression can include promoters, introns, enhancer sequences, termination sequences, response elements, or inducible elements that modulate expression of a BRI nucleic acid. Elements necessary for expression can be of bacterial, yeast, insect, mammalian, or viral origin and constructs can contain a combination of elements from different origins.

As used herein with respect to promoter and/or other regulatory element(s), operably linked means that such sequences are positioned in a construct relative to a BRI nucleic acid molecule in such a way as to direct or regulate expression of the BRI nucleic acid molecule. Operably linked also refers to an in-frame junction between a BRI nucleic acid sequence and a heterologous nucleic acid sequence such that a correct (i.e., in frame) BRI-heterologous polypeptide fusion protein is produced following transcription and translation of the sequences. It is a feature of the invention that the BRI-heterologous polypeptide fusion protein contains a dibasic cleavage site, preferably at or near the junction between the BRI polypeptide and the heterologous polypeptide. For convenience, the sequence of a cleavage site can be derived from the BRI nucleic acid molecule (e.g., one encoding 243 amino terminal residues of human $BRI_2$). In one embodiment, a dibasic cleavage site is a Lysine-Arginine sequence.

Many methods can be used to introduce a nucleic acid into a cell. In fact, many methods for introducing nucleic acid into cells, whether in vivo or in vitro, are well known to those skilled in the art. For example, calcium phosphate precipitation, electroporation, heat shock, lipofection, microinjection, and viral-mediated nucleic acid transfer are common methods for introducing nucleic acid into cells. In addition, naked DNA can be delivered directly to cells in vivo as described elsewhere. See, for example, U.S. Pat. Nos. 5,580,859 and 5,589,466.

A variety of promoter sequences can be used to control expression of a BRI nucleic acid molecule. These include the metallothionine (MT) promoter from which expression can be regulated through modulation of zinc and glucocorticoid hormone levels (Palmiter, et al., *Nature* 300, 611-615 (1982)); the rat neuron specific enolase gene promoter (Forss-Petter, et al., *Neuron* 5; 197-197 (1990)); the human β-actin gene promoter (Ray, et al., *Genes and Development* (1991) 5:2265-2273); the human platelet derived growth factor B (PDGF-B) chain gene promoter (Sasahara, et al., *Cell* (1991) 64:217-227); the rat sodium channel gene promoter (Maue, et al., *Neuron* (1990) 4:223-231); the human copper-zinc superoxide dismutase gene promoter (Ceballos-Picot, et al., *Brain Res.* (1991) 552:198-214); and promoters for members of the mammalian POU-domain regulatory gene family (Xi et al., (1989) *Nature* 340:35-42).

Of particular interest are regulatory sequences derived from a gene encoding a prion protein such as mouse or human prion regulatory sequences. It is preferred that the prion promoter is functional in the brain of the host animal. Prion proteins are implicated in the pathogenesis and transmission of Gerstmann-Straussler syndrome in humans, and scrapie, an equivalent non-human animal disease. As appropriate, prion promoter sequences can be amplified using PCR procedures known to those skilled in the art. Prion promoter sequences are described in Basler, et al. (1986), *Cell* 46:417-428 and Scott, et al. (1992) *Protein Science* 1:986-987 and in, for example, GenBank Accession Nos. AJ289875 and D26150. In some instances, a probe is employed to obtain a prion promoter using, for example, hybridization techniques as described above.

Due to the high conservation of actin sequences between organisms, and due to the high level of expression of actin genes, promoter and/or regulatory sequences from actin genes also are useful in the constructs of the invention. Actin is the most abundant protein in eukaryotic cells and of all the cytoskeletal proteins, and often constitutes 5% or more of the total cellular protein. Actin genes have been highly conserved in evolution. Muscle and non-muscle actins, for example, differ in fewer than 7% of their amino acids. Actin molecules from widely divergent sources have been shown to be functionally interchangeable in vitro. The sequence of representative actin promoters can be found in GenBank and include Y00474 or E06566 from human, D11039 from *T. thermophila*, X15730 and K01489 from Drosophila, X76381 from Xenopus, J01297 from soybean, and S44221 from rice. A preferred actin promoter is from chicken (e.g., GenBank Accession Nos. E02199, E02194 and E01452).

Figure 4:
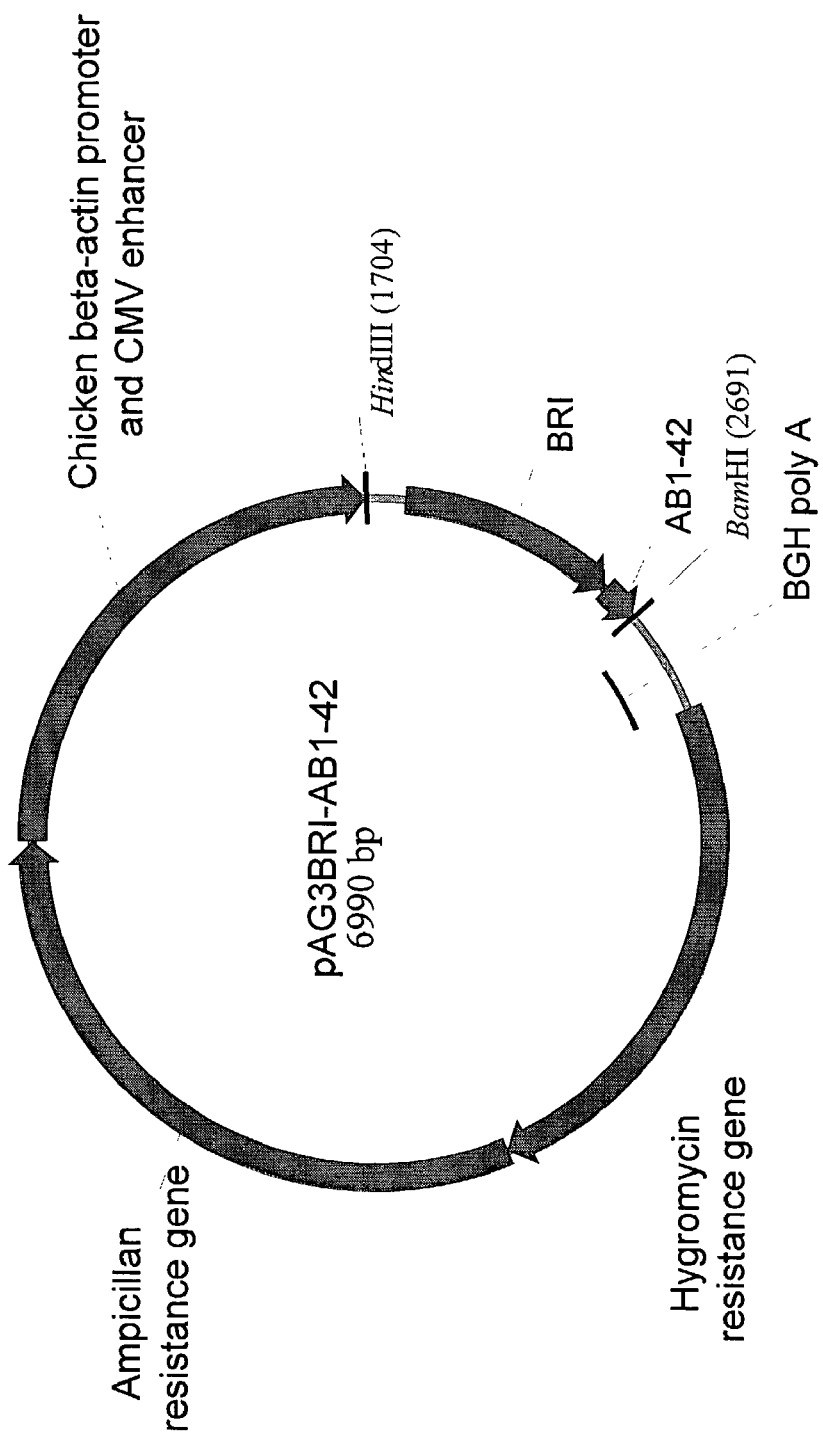
FIG. 4 is a restriction map of pAG3BRI-Aβ1-42.

FIGS. 2 and 3 are the nucleotide coding sequences and amino acid sequences showing a representative operable linkage between a BRI sequence and an Aβ heterologous sequence (from pAG3BRI-Aβ1-40 and pAG3BRI-Aβ1-42, respectively). FIG. 4 shows a restriction map of a representative construct of the invention. In this embodiment, the construct contains a chick β-actin promoter operably linked to a BRI nucleic acid molecule, which is operably linked to a heterologous nucleic acid molecule (i.e., Aβ1-42).

Methods of Directing a Polypeptide Through the Secretory Pathway of a Cell

The invention also features methods of directing a heterologous polypeptide through the secretory pathway of a cell by introducing a construct of the invention into a cell. Such a construct includes a promoter operably linked to the 5' end of a first nucleic acid molecule encoding an amino terminal region of a BRI polypeptide which is, in turn, operably linked to the 5' end of a second nucleic acid molecule encoding a heterologous polypeptide. Expression of the construct in the cell results in a BRI-heterologous polypeptide fusion protein. Because of the BRI polypeptide sequence, the BRI-heterologous polypeptide fusion protein moves through the secretory pathway of the cell and can be deposited in the membrane. The heterologous polypeptide can be a diagnostic polypeptide or a therapeutic polypeptide.

Cells into which a construct of the invention can be introduced include, but are not limited to, CHO cells, 293 cells, COS cells, H4 neuroglioma cells, and C17-2 cells. In certain embodiments, it is desirable to direct a heterologous polypeptide through the secretory pathway of one or more cells in vivo, for example, in an animal (e.g., a mouse, a rat, a guinea pig, or a human) for therapeutic purposes. A construct can be administered to an animal by a variety of routes such as intraperitoneally, intramuscularly, intranasally and transdermally. Administration by such routes is routine and uses art-known methods. Constructs of the invention can be administered with a pharmaceutically acceptable carrier appropriate for the intended route such as sterile water, buffers, physiological saline, and artificial cerebral-spinal fluid. See, *Remington's Pharmaceutical Sciences*, Mack Publishing Co., Easton, Pa., 16$^{th}$ Ed., 1982

The BRI-heterologous polypeptide fusion protein can be cleaved by a PC while moving through the secretory pathway or at the membrane. In an in vivo embodiment of the invention, the heterologous polypeptide is cleaved and is subsequently delivered to the vascular system of the animal. From the vascular system, the heterologous polypeptide can enter the circulatory and/or lymphatic systems. Processing of the heterologous polypeptide in such a way can ultimately elicit an immune response directed toward the heterologous polypeptide. Accordingly, a heterologous polypeptide can be used therapeutically as, for example, a vaccine. If desired, the construct also can include a third nucleic acid molecule encoding an immunogenic tag operably linked to the heterologous nucleic acid to further stimulate the immune response. Representative immunogenic tags include the cytokines discussed above. Additional sequences exhibiting immunogenicity are known in the art (e.g., CTLA-4).

Methods for detecting nucleic acid or the product of a nucleic acid in cell culture (e.g., secreted into medium) or in biological samples are known to those of skill in the art. Transcription of nucleic acid sequences can be detected by Northern blotting. Immunoassay formats such as those disclosed herein (ELISA, immunoprecipitation-mass spectrometry (IP-MS), and Western blots) can be used to detect the polypeptide product of the heterologous nucleic acid molecule and are well known in the art. See, *Short Protocols in Molecular Biology*, Ch. 11, John Wiley & Sons, Ed., Ausubel et al., 1992. In addition to ELISA, solid-phase immunoassays include competition immunoassays, immobilized-antigen immunoassays, immobilized-antibody immunoassays, and double-antibody immunoassays. Further, several types of mass spectrometry (MS) are available and routinely used in the art, and include Fourier-transform MS, Ion-trap MS, Magnetic-sector MS, Quadropole MS and Time-of-flight (TOF) MS.

Detection of nucleic acids or polypeptides in vitro or in vivo is usually via a label, e.g., a radioactive label (e.g., $^{3}$H, $^{125}$I, $^{131}$I, $^{32}$P, $^{35}$S, and $^{14}$C) or a non-radioactive label (e.g., a fluorescent label, a chemiluminescent label, a paramagnetic label, or an enzyme label) using techniques known to those of ordinary skill in the art. Examples of enzyme labels used routinely in the art for detection and quantitation include horseradish peroxidase (HRP) and alkaline phosphatase (AP). The substrates available for either HRP or AP labels are known in the art and can be selected based upon the desired method of detecting complex formation (e.g., a fluorogenic, chemiluminescent or calorimetric signal).

In one embodiment, the heterologous polypeptide is Aβ. Methods of detecting Aβ are well known in the art, and can include using a highly specific sandwich ELISA (Suzuki et al., 1994, *Science*, 264:1336-40; Asami-Odaka et al., 1995, *Biochem.*, 34:10272-8). In such an ELISA, a BAN-50 antibody can be used, which specifically captures Aβ polypeptides at the N-terminus, followed by either a BA-27 antibody, which detects only Aβ1-40, or a BC-05 antibody, which detects only Aβ1-42.

In addition, suitable antibodies that detect an epitope within Aβ (or within the Aβ portion of APP) are also commercially available from a variety of sources, including, but not limited to, Biosource International (Camarillo, Calif.), Senetek PLC (London, England), Zymed Laboratories (San Francisco, Calif.), Peninsula Laboratories (San Carlos, Calif.) and Boehringer Mannheim (Indianapolis, Ind.). In addition, BNT-77 is an antibody that captures rodent Aβ, (Asami-Odaka et al., 1995, *Biochem.*, 34:10272-8) and can be used in conjunction with the BA-27 or BC-05 antibodies described above. By way of example, Ciphergen (Fremont, Calif.) sells a biochip system for capturing Aβ polypeptides from culture medium or a biological sample and utilizes Surface-Enhanced Laser Desorption/Ionization technology (SELDI) with Time-of-flight mass spectrometry (TOF-MS) to detect and quantitate the level of an Aβ polypeptide.

Neuritic plaques in the brain of an individual with AD or in an animal model of AD (e.g., a transgenic animal) can be detected and/or monitored in vivo using an Aβ polypeptide covalently modified with a polyamine (e.g., putrescine, spermidine, or spermine) (Wengenack et al., 2000, *Nat Biotechnol.*, 18:868-72). A radiolabeled polyamine-modified Aβ polypeptide can be administered to an individual intravenously and detected using standard methods. For example, a radiolabel suitable for diagnostic imaging can be used (e.g., $^{123}$I) and detected using single photon emission computed tomography (SPECT).

Secretory Pathway

The invention provides BRI constructs and methods of using BRI constructs of the invention for directing a heterologous polypeptide through the secretory pathway of a cell. Movement of a heterologous polypeptide through the secretory pathway of a cell increases the likelihood of proper folding and assembly. In an embodiment of the invention, the BRI-heterologous polypeptide fusion protein is deposited in the cell membrane, preferably with the C-terminal region (i.e., the heterologous polypeptide portion) extracellular. The following is a brief overview of how newly synthesized BRI-heterologous polypeptide fusion proteins can be delivered to their target locations via the secretory pathway.

The entry station for proteins of the secretory pathway (e.g., secretory proteins, plasma membrane proteins and proteins destined for various compartments of the endomembrane system) is the endoplasmic reticulum (ER). Targeting of the nascent BRI-heterologous polypeptide fusion protein to the ER membrane usually is by a hydrophobic signal sequence. The signal sequence can interact with a signal recognition particle complex, and the BRI-heterologous polypeptide fusion protein can be translocated across the ER membrane to the ER lumen or inserted into the ER membrane. On the luminal site of the ER various chaperones can associate with the fusion protein in order to control and support correct folding. In addition, the newly synthesized fusion protein undergoes co- and post-translational processing, e.g., glycosylation, disulfide bond formation, and oligomerization.

Polypeptide transport from the ER to the Golgi complex involves the ER-Golgi intermediate compartment (ERGIC). En route through the secretory pathway, the fusion protein can enter the Golgi at its cis-side (cis-Golgi network, CGN). Proteins continue their passage through the several subcompartments of the Golgi (CGN, cis-, medial-, trans-Golgi and trans-Golgi network (TGN)), where they are subjected to various kinds of post-translational processing, e.g., remodeling of the N- and O-linked oligosaccharide side chains. The exit site of the Golgi, the trans-Golgi network (TGN), is a highly variable structure that differs with different cell types, and it has been suggested that the TGN itself is composed of functionally distinct subdomains that might be involved in sorting polypeptides into different types of transport vesicles destined for endosomes, lysosomes, secretory granules and the plasma membrane.

Movement through the secretory pathway requires packaging of the protein or polypeptide in a vesicle that can bud from a donor compartment and fuse with an acceptor compartment. Three major types of protein-coated transport vesicles have been characterized in molecular detail, and can be assigned to various steps in the secretory pathway: COPII-coated vesicles allow exit from the ER, COPI-coated vesicles carry proteins within the early secretory pathway, i.e., between the ER and the Golgi apparatus, and clathrin-coated vesicles mediate transport from the TGN.

Once through the entirety of the secretory pathway, the fusion protein can be cleaved by a PC in the TGN or at the membrane during or following deposition. If the cell is in vivo, for example, in an animal, the secreted heterologous polypeptide is delivered to the vascular system and from there enter the circulatory and/or lymphatic systems. Recent evidence indicates that the vascular system mediates exchange between the vascular space and other systems (e.g., circulatory, and lymphatic). The exchange can occur through differentiated microdomains of vascular endothelium such as fenestrae. The microdomains are differentiated with regard to surface charge, protein distribution within the lipid bilayer, membrane fluidity and other features. The exchange is also affected by characteristics of the molecule to be transported such as molecular size, charge, shape and its carbohydrate content. Methods of exchange across cells include (a) receptor-mediated transcytosis, and (b) fluid-phase endocytosis. The molecule can become modified in transit, which can determine its destination and subsequent metabolism. Using a BRI construct of the invention to produce a BRI-heterologous polypeptide fusion protein, a heterologous polypeptide can be directed through the secretory pathway of a cell, thereby increasing the likelihood of proper folding and assembly. Further, in an in vivo environment, the heterologous polypeptide can be efficiently directed through the secretory pathway and delivered into the vascular, circulatory, and/or lymphatic systems of an animal.

Transgenic Animals

The invention additionally features transgenic non-human animals whose genome comprises a construct of the invention. Constructs of the invention as well as the individual components of the constructs are discussed above. The invention is directed to a transgenic non-human animal, preferably a rodent, such as a mouse, a rat, a guinea pig, or other animal together with methods and compositions for preparing and using such an animal. As used herein, a transgenic animal is an animal that has an introduced nucleic acid in its genome. Typically, the introduced nucleic acid is exogenous, i.e., from a source different than that from which the introduced nucleic acid was derived. One of the phenotypes of the animal is that it expresses a BRI-heterologous polypeptide fusion protein at a level such that the amino terminal region of the BRI polypeptide, the heterologous polypeptide, or the fusion protein is detectable in biological or tissue samples from the animal (e.g., blood, urine, cerebrospinal fluid, or skin) using, for example, methods disclosed herein.

A construct of the invention can be introduced into an animal at an embryonic stage, preferably the one cell stage, or fertilized egg stage, and generally not later than about the 8-cell stage. The zygote or embryo is then carried to term in a pseudo-pregnant female that acts as a surrogate mother. By a pseudo-pregnant female is meant a female in estrus who has mated with a vasectomized male; she is therefore competent to receive embryos but does not contain any fertilized eggs. In order to achieve stable inheritance of the introduced nucleic acid, the integration event must occur in a cell type that can give rise to functional germ cells (i.e., sperm or oocytes). Two animal cell types that can form germ cells and into which DNA can be introduced readily are fertilized egg cells and embryonic stem (ES) cells. Methods of producing transgenic animals using zygote injection is described, for example, in U.S. Pat. No. 4,736,866 and methods of producing transgenic animals using ES cells is described, for example, in U.S. Pat. Nos. 4,396,601 and 4,497,796. Using the construct of the present invention, the transgene initially includes both the BRI amino terminal region and a heterologous polypeptide fused in-frame.

Nuclear transplantation also can be used to generate non-human animals of the invention. For example, fetal fibroblasts can be genetically modified such that they contain a construct of the invention and express a BRI-heterologous polypeptide fusion protein, and then such cells can be fused with enucleated oocytes. After activation of the oocytes, the eggs are cultured to the blastocyst stage, and implanted into a recipient. See, Cibelli et al., *Science*, (1998) 280:1256-1258. Adult somatic cells including, for example, cumulus cells and mammary cells, can be used to produce animals such as mice and sheep, respectively. See, for example, Wakayama et al., *Nature*, (1998) 394:369-374; and Wilmut et al., Nature, (1997) 385:810-813. Nuclei can be removed from genetically modified adult somatic cells, and transplanted into enucleated oocytes. After activation, the eggs can be cultured to the 2- to 8-cell stage, or to the blastocyst stage, and implanted into a suitable recipient. Wakayama et al., 1998, supra.

Heterologous polypeptide levels, RNA expression, and transgene copy number can be determined in weanling animals (4-5 weeks) using methods known to those of skill in the art (e.g., hybridization or PCR techniques as described above). When a constitutively active promoter such as a prion promoter is used, changes in levels of RNA expression from the introduced nucleic acid are not expected in animals beyond weanling age. When a developmentally- and/or tissue-specific promoter is used, RNA and/or protein levels can be monitored to determine expression levels in different developmental stages and/or tissues. The transgenic animals also can be observed for behavioral changes such as poor mating response, agitation, diminished exploratory behavior in a novel setting, inactivity, or seizures. Standard physiological tests also can be performed on such transgenic animals, such as a complete blood count (CBC) and glucose uptake.

Parameters that can influence the phenotype of transgenic animals include the host strain, the site of integration of the construct, the number of constructs integrated and the level of expression of the heterologous nucleic acid. The animals used as a source of fertilized eggs or embryonic stem (ES) cells, i.e., the host animal, can be any animal, although generally the preferred host animal is one that lends itself to multigenerational studies. Another preferred characteristics of a host animal includes longevity to the extent that there is sufficient time for observable physiological and/or pathological changes to occur in the animal. Of particular interest as host animals are rodents including mice, such as mice of the FVB strain and commercially available strains such as the C57B6× SJL.F1 hybrid and the Swiss Webster×C57B16/DB2 hybrid. Other strains and hybrids can be evaluated using the techniques described herein. In some instances, however, a primate, for example, a rhesus monkey may be desirable as a host animal, particularly for evaluation of therapeutic treatments relative to the heterologous polypeptide. It can be appreciated by those of skill in the art that sufficient copies of a transgene and/or a sufficient level of expression of a transgene will result in a measurable biochemical change in relevant physiological structures and may subsequently result in detectable clinical and/or behavioral symptoms.

Transgenic animals in which the heterologous polypeptide is an Aβ polypeptide can exhibit impaired performance in memory and learning tests and abnormal neuropathology in a cortico-limbic region of the animal's brain. Impaired performance and the abnormal neuropathology are in comparison to a control animal lacking the construct or expressing a full-length BRI nucleic acid molecule. Such abnormal neuropathology can be the presence of immunoreactive β-amyloid deposits; an elevated number of thioflavin S-positive β-amyloid deposits; an increased amount of thioflavin S-positive β-amyloid deposits; hypertrophic gliosis in the cortico-limbic structures of the brain; diminution of 2-deoxyglucose uptake in the cortico-limbic structures; and diminution of 2-deoxyglucose utilization in the cortico-limbic structures. The gliosis and clinical manifestations in affected transgenic animals are indicative of a true neurological disease. In certain embodiments, the animal develops a progressive neurological disorder within a short period of time from birth, generally within a year from birth, oftentimes within 2 to 6 months from birth. The progressive aspects of the neurological disease are characterized by diminished exploratory and/or locomoter behavior and diminished 2-deoxyglucose uptake/utilization and hypertrophic gliosis in the cortico-limbic regions of the brain. Further, the changes that are seen are similar to those that are seen in Tg2576 mice (see, for example, U.S. Pat. No. 5,877,399) as well as aging animals.

The present invention offers several advantages over existing models for progressive neurological disorders such as AD. While current animal models are extremely valuable tools to study Aβ deposition and APP processing (for example, Hsiao, 1995, *Neurobiol. Aging*, 16:705-6; Hsiao et al., 1995, *Neuron*, 15:1203-18; Duff et al., 1996, *Nature*, 383:710-3; Carlson et al., 1997, *Hum. Mol. Genet.*, 6:1951-9; Sturchler-Pierrat et al., 1997, *Proc. Natl. Acad. Sci. U.S.A.*, 94:13287-92; Zhang et al., 1997, *J. Neurosci.*, 17:7655-61; Holcomb et al., 1998, *Nat. Med.*, 4:97-100; Iadecola et al., 1999, *Nat. Neurosci.*, 2:157-61; and Chapman et al., 1999, *Nat. Neurosci.*, 2:271-6), the level of mutant APP overexpression needed to achieve amyloid deposition may confound interpretations of pathological and behavioral studies. Not only can mutant APP overexpression artificially contribute to some of the pathological and behavioral changes that have been described, it is also possible that overexpression of APP and subsequent production of the neuroprotective sAPP derivative may paradoxically prevent these models from fully recapitulating AD pathology. The ability to direct an Aβ or other heterologous polypeptide through the secretory pathway of cells in vivo using a BRI-containing construct provides an effective method to move such polypeptides out of the cell and process them.

The invention will be further described in the following examples, which do not limit the scope of the invention described in the claims.

EXAMPLES

Example 1

Production of BRI Fusion Constructs

PCR primers were designed to generate a 991 base pair fragment of the BRI gene using human brain library cDNA as template. The forward primer, 5'-TTC CCT CGA GTC TCA GCC GCC CGG AGC-3' (SEQ ID NO:5), and the reverse primer, 5'-ACT GCT CGA GAT GTA AAG GGT GGG GTT ATG-3' (SEQ ID NO:6), included the recognition sequence for the restriction enzyme XhoI in their 5' sequence. The amplified product was then digested with XhoI to create a fragment suitable for cloning into pBS (KS−). The sequence of the construct was confirmed by direct sequencing on an ABI 377 automated sequencer using Big Dye chemistry and Sequence Navigator software (Perkin-Elmer). This construct was used as the template for the subsequent PCR reactions.

Subsequently, fusion constructs encoding the first 243 amino acids of BRI followed by either Aβ1-40 (BRI-Aβ1-40) or Aβ1-42 (BRI-Aβ1-42) were generated by PCR amplification. The amino terminal portion encoding BRI was amplified using the wild-type BRI cDNA as template and the primers BRI-for (5'-ATT TTT AAG CTT CTC GAG AGG CTG CAA TCG CAG CGG GAG-3' (SEQ ID NO:7)) and BRI-rev (5'-GTC GGA ATT CTG CAT CAC GTT TCT GAA TAC CTT TAA TAG TTT C-3' (SEQ ID NO:8)). cDNAs encoding Aβ1-40 and Aβ1-42 were amplified using APP 695 wild-type cDNA as template and the primers Aβ-for (5'-TGG AGA TCT GAT GCA GAA TTC CGA CAT GAC TC-3' (SEQ ID NO:9)) and Aβ1-40-rev (5'-TAA AAG GAT CCC TAG ACA ACA CCG CCC ACC ATG AG-3'(SEQ ID NO:10)) and Aβ1-42-rev (5'-TAA AAG GAT CCC TAC GCT ATG ACA ACA CCG CCC ACC ATG AG-3' (SEQ ID NO:11)). These PCRs were performed using the High Fidelity PCR kit from Roche. The resultant BRI-encoding cDNA was digested with HindIII and EcoRI while the Aβ-encoding cDNAs were digested with EcoR1 and Bam H1. The fragments were ligated into a pAG3 expression vector using a three-way ligation that resulted in an in-frame fusion of the BRI and the Aβ sequences, to produce pAG3BRI-Aβ1-40 and pAG3BRI-Aβ1-42. Sequences were confirmed by automated DNA sequencing. Transfection of cells, Aβ ELISAs, and immunoprecipitation-mass spectrometry (IP/MS) were carried out as described (Murphy et al., 1999, *J. Biol. Chem.*, 274:11914-23). Western blotting was carried out as described using BAN50, BC05 and BA27 antibodies at 1:1000 (Suzuki et al., 1994, *Science*, 264:1336-40). An anti-BRI antibody, EN3, raised in rabbit and directed toward the sequence YKLQR- RETIKGIQ (corresponding to amino acids 229-241 of BRI; SEQ ID NO:12) was also used at a dilution of 1:1000.

Example 2

In Vitro Expression of the BRI-Aβ Fusion Protein

To determine whether the pAG3BRI-Aβ fusion proteins produce Aβ, conditioned media from human embryonic kidney cells (293T) and mouse CNS progenitor cells (C17-2) (Snyder et al., 1992, *Cell,* 68:33-51) transiently transfected with pAG3BRI-Aβ1-40 and pAG3BRI-Aβ1-42 was analyzed using end specific Aβ ELISAs. These data indicated that Aβ1-40 was selectively produced from the pAG3BRI-Aβ1-40 construct and that Aβ1-42 was selectively produced from the pAG3BRI-Aβ1-42 construct (Table 1). To further investigate the expression of Aβ from these constructs, stably transfected H4 neuroglioma cells were generated. As with the transient transfections, each BRI fusion construct resulted in selective overexpression of the particular Aβ peptide (Table 1), with over 98% of the Aβ generated ending with the appropriate amino acid. The production of Aβ from the BRI fusion constructs was also compared to that generated by 2b7 cells and CHO-APP695NL,I,his cells. The 2b7 clonal CHO line secretes the highest levels of Aβ of any wild type APP transfected line generated by the inventors. The CHOAPP695NL, I,his cells also express the highest level of Aβ from any stable cell line generated by the inventors, presumably because the NL mutation increases Aβ1-40 and Aβ1-42 production whereas the V717I substitution increases the proportion of Aβ1-42. Significantly, the specific levels of Aβ1-40 or Aβ1-42 were much higher using the BRI fusion methodology.

To obtain final confirmation of the selectivity of Aβ secretion from this system, IP/MS analysis of the media was performed. As shown in FIGS. 1A and 1B, the mass spectra demonstrate that each construct results in the selective overexpression of the appropriate full length Aβ peptide with negligible increase in any other peptide peaks. FIG. 1A shows that no Aβ1-42 is detected by IP/MS and that only minor amounts of smaller Aβ peptides (Aβ1-32, Aβ1-34, Aβ1-37 and Aβ1-39) are detected. The shoulder on the 1-40 peak corresponds to the Aβ1-40 peptide complexed with a sodium ion. The levels determined by ELISA analysis of this media are shown in Table 1 (H4/pAG3BRI-Aβ1-40). IP/MS analysis as shown in FIG. 1B reveals that Aβ1-42 represents the vast majority of Aβ produced by this construct. Aβ levels determined by ELISA analysis of this media are shown in Table 1 (H4/pAG3BRI-Aβ1-42). In vector transfected H4 cells, only a small peak corresponding to Aβ1-37 is detected by IP/MS.

Western blot analysis of the H4 stable lines expressing the pAG3BRI-Aβ fusion proteins using antibodies to the amino terminus of Aβ, Aβ1-40, Aβ1-42, and BRI indicates that fusion proteins containing the expected epitopes and of the appropriate size (~36 kDa) are produced by expression of the pAG3BRI-Aβ constructs.

TABLE 1

ELISA analysis of cells transfected with BRI-Aβ fusion constructs

| Cell line/DNA | Transfection[b] | Aβ1-40 (pM)[c] | Aβ1-42 (pM)[d] | % Aβ1-40 | % Aβ1-42 |
|---|---|---|---|---|---|
| 293T/pAG3[a] | Transient | 11 ± 3 | 0 | 100% | 0% |
| 293T/pAG3BRI-Aβ1-40 | Transient | 145 ± 8 | 0 | 100% | 0% |
| 293T/pAG3BRI-Aβ1-42 | Transient | 8 ± 2 | 161 ± 13 | 5% | 95% |
| C17-2/pAG3 | Transient | 8 ± 1 | 2 ± 1 | 80% | 20% |
| C17-2/pAG3BRI-Aβ1-40 | Transient | 383 ± 26 | 2 ± 1 | 99% | 1% |
| C17-2/pAG3BRI-Aβ1-42 | Transient | 12 ± 3 | 475 ± 64 | 2% | 98% |
| H4/pAg3 | Stable | 31 ± 5 | 4 ± 1 | 89% | 11% |
| H4/pCDNA3APP695 | Stable | 694 ± 38 | 94 ± 3 | 88% | 12% |
| H4/pAG3BRI-Aβ1-40 | Stable | 18735 ± 177 | 173 ± 28 | 99% | 1% |
| H4/pAG3BRI-Aβ1-42 | Stable | 629 ± 9 | 28059 ± 159 | 2% | 98% |
| (2b7) CHO/pAG3APP695wt | Stable | 3421 ± 420 | 392 ± 28 | 90% | 10% |
| CHO/pAG3APP695NL,I,his | Stable | 12861 ± 1809 | 2902 ± 395 | 81% | 19% |

[a]The pAG3 vector has been described (Murphy et al., 1999, J. Biol. Chem., 274:11914-23).
[b]Transient transfections were performed in triplicate in 6 well plates using Fugene 6 (Roche). Stable lines were transfected with Fugene 6 and selected with either hygromycin (pAG3) or G418 (pCDNA3). Each stable line was derived from a single colony that was selected based on high-level expression.
[c]Aβ1-40 was assayed using a 3160/BA27 ELISA.
[d]Aβ1-42 was assayed using a 3160/BC05 ELISA. The small amount of Aβ1-40 detected above background cells transfected with pAG3BRI-Aβ1-42 is likely due to the fact that the Aβ1-40 "specific" BA-27 antibody will detect Aβ1-42 at low efficiencies (~1%). A similar cross-reactivity is likely to account for the small amount of Aβ1-42 detected in the pAG3BRI-Aβ1-40 transfects. In all cases, media samples were conditioned for 16 hrs.

Example 3

Production of Transgenic Mice

For microinjections, purified, linearized pAG3BRI-Aβ1-40 and pAG3BRI-Aβ1-42 constructs were diluted to a final concentration of 3-10 ng/μl in injection buffer. DNA was then injected into embryos from B6/D2× Swiss Webster parents. ~100 potential founders were generated for each line. Founder mice were screened by PCR at 2 wks of age for integration of the transgene and PCR positive mice were confirmed by Southern blot. In addition, plasma from the mice was screened for Aβ by ELISA. Plasma Aβ is a good predictor of CNS expression in mice expressing APP under control of the MoPrP promoter.

Those founder mice that have a high copy number of the pAG3BRI-Aβ transgene, high plasma levels of Aβ, or both, are bred by crossing to Swiss Webster mice. 2-month old F1 offspring are used for analysis. At sacrifice, the brains of transgene-positive and -negative F1 progeny are divided by midsagittal dissection. Brain hemisections are homogenized in 2% SDS, diluted appropriately, and Aβ levels (pmol/mg) determined by ELISA. For comparison of Aβ levels, SDS brain homogenates from 2-month old Tg2576 mice are analyzed in parallel. pAG3BRI-Aβ transgenic animals expressing at least 40-50% of the level of Aβ1-42 and >5-10% the level of Aβ1-40 found in the brain homogenates of 2-month old Tg2576 mice are further characterized (using tissue from the other half of the brain) by Northern blotting to assess transgenic RNA expression levels and Western blotting to assess protein levels.

Once several high expressing lines of pAG3BRI-Aβ1-40 and pAG3BRI-Aβ1-42 mice are identified, the expression pattern of the pAG3BRI-Aβ construct is further characterized in these lines both by in situ hybridization analysis and immunohistochemical analysis. The lines that are chosen for further study are bred in sufficient numbers for an ageing study. pAG3BRI-Aβ1-40 and pAG3BRI-Aβ1-42 lines are bred to homozygosity to facilitate analysis. In addition, a pAG3BRI-Aβ1-40+pAG3BRI-Aβ1-42 line is generated by crossing a high expressing pAG3BRI-Aβ1-40 homozygote with a high-expressing pAG3BRI-Aβ1-42 homozygote. pAG3BRI-Aβ1-40 and pAG3BRI-Aβ1-42 mice, non-transgenic littermates, and pAG3BRI-Aβ1-40+pAG3BRI-Aβ1-42 mice are sacrificed at varying ages (e.g., 2, 6, 9, 12 and 18 months; 6-10 per group). Brains are rapidly removed and hemisected. One hemisphere is used for Aβ ELISA and the other for immunohistochemistry. Prior to sacrifice, those mice also are evaluated for behavioral dysfunction using a T-maze testing paradigm.

Example 4

Brain Tissue Preparation

Frozen hemibrains are sequentially extracted in a 2-step procedure involving sonication in (i) 2% SDS and (ii) 70% formic acid. After each sonication, the samples are centrifuged (100,000×g for 1 hr at 4° C.), the supernatant recovered, and the pellet sonicated with the next solution. For Aβ ELISA, the 2% SDS extracts are diluted at least 1:40, and formic acid extracts neutralized by a 1:20 dilution into 1 M Tris phosphate buffer (pH 8.0). Fmoles/ml are calculated by comparing the sample absorbance to the absorbance of known concentrations of synthetic Aβ1-40 or Aβ1-42 in identical solution as the samples, and these values are corrected with the wet weight of the original homogenate so that they are finally expressed as pmol/gram wet weight.

To assess amyloid burden immunohistochemically, sections from tissue samples fixed in 4% paraformaldehyde in 0.1 M phosphate buffer (PB, pH 7.6) are stained for Aβ deposition as follows using antibodies specific for Aβ1-40 (BA27), Aβ1-42 (BC05) or total Aβ (4G8). Paraffin sections (5 βm) with and without 70% formic acid pretreatment are incubated with 2% blocking serum in PBS for one hour, then with primary Aβ antibodies (BA-27, 0.4 μg/ml; BC-05, 0.1 μg/ml, or 4G8, 0.5 μg/ml) overnight. The sections are stringently washed and incubated with horseradish peroxidase conjugated to a secondary antibody (1:2000) for one hour and the immunoreactivity visualized by incubation with 0.03% 3,3'-diaminobenzidine or nickel enhanced diaminobenzidine. Sections from AD brains are stained in parallel as controls. Amyloid burden is assessed as described by Gomez-Isla et al. (*Annals of Neurology*, 41:17-24, 1997).

Example 5

Aβ Levels in Transgenic Mice Expressing BRI-Aβ40 or BRI-Aβ42

Figure 5:
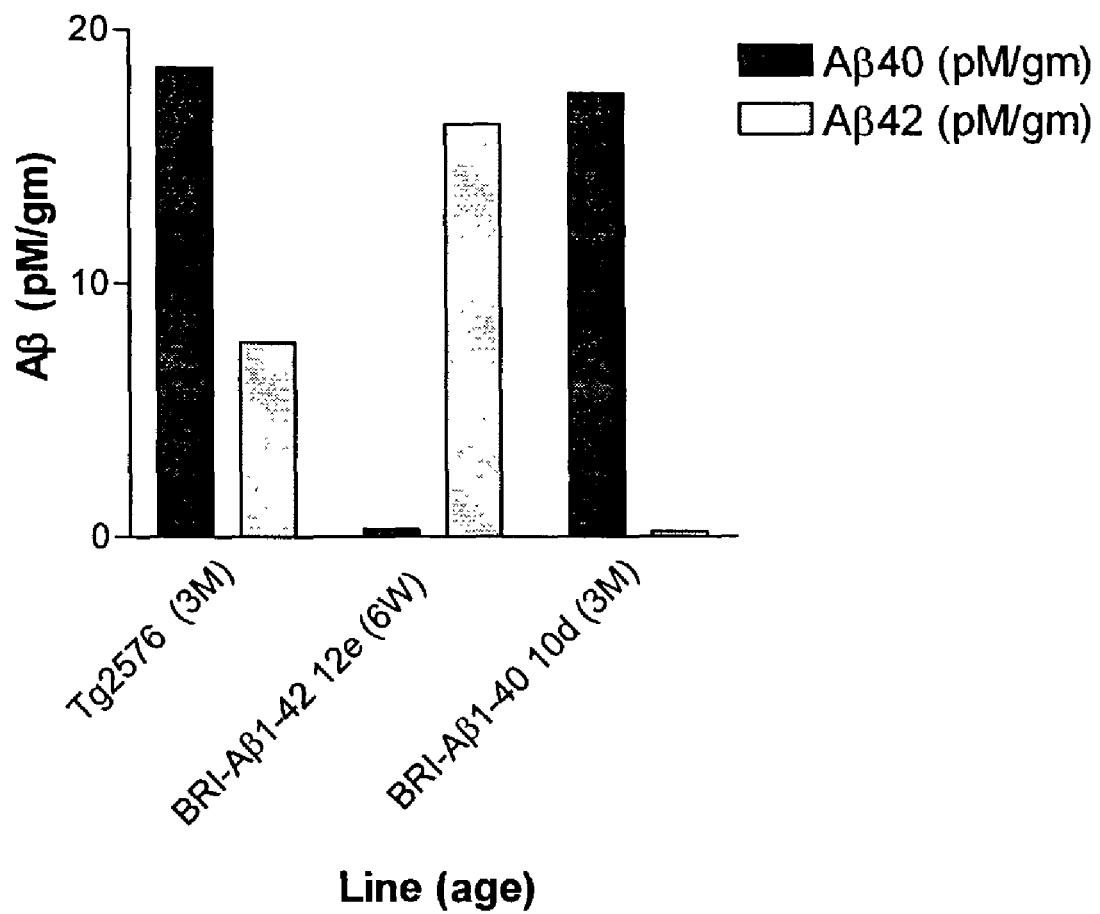
FIG. 5 is a graph showing analysis of total Aβ in pAG3BRI-Aβ transgenic mice as measured by ELISA. 6W refers to 6 weeks; 3M refers to 3 months.

Brains were harvested from pAG3BRI-Aβ1-42 mice (line 12e; n=2) or pAG3BRI-Aβ1-40 mice (line 10d; n=1). AP ELISAs showed that these lines selectively overexpress the appropriate Aβ polypeptide (FIG. 5). Each of these mice lines produce levels of the specific Aβ that are comparable to Tg2576 mice, which overexpress APP695NL (Mullan et al., 1992, *Nat. Gen.*, 1:345-7) and overproduce both Aβ1-40 and Aβ1-42 (FIG. 5). Aβ deposits will develop in the pAG3BRI-Aβ1-40 and pAG3BRI-Aβ1-42 mice in a manner similar to Tg2576 mice.

Example 6

DNA Vaccination with a pAG3BRI-Aβ1-40 or pAG3BRI-Aβ1-42

Figure 6:
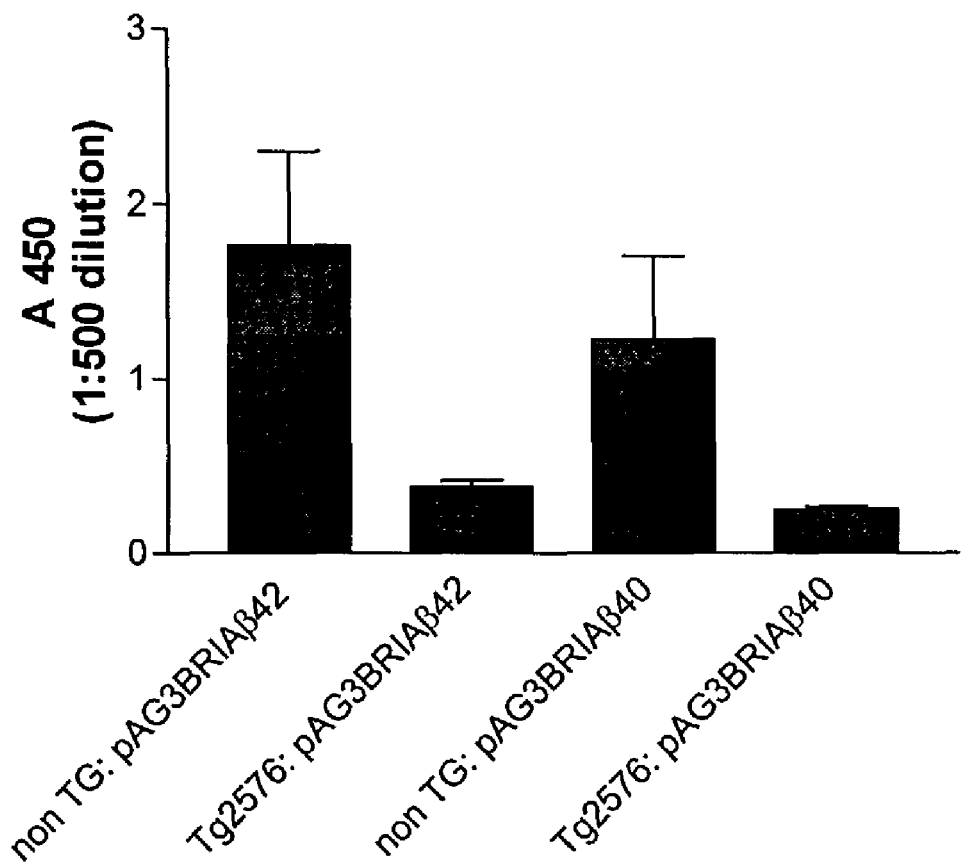
FIG. 6 is a graph showing anti-Aβ titers in mice immunized with pAG3BRI-Aβ nucleic acid constructs.

Studies were performed to determine if pAG3BRI-Aβ fusion constructs can be used as DNA vaccines. pAG3BRI-Aβ1-40 or pAG3BRI-Aβ1-42 fusion constructs were resuspended in phosphate buffered saline (pH 7.0) (PBS) and injected intramuscularly (50 μg/dose). 3 weeks after the initial immunization, pAG3BRI-Aβ1-40 or pAG3BRI-Aβ1-42 fusion constructs were again administered intramuscularly (50 μg/dose). Antibody response against Aβ was measured 3 weeks after the last immunization. Results, graphically shown in FIG. 6, demonstrate that the pAG3BRI-Aβ1-40 or pAG3BRI-Aβ1-42 nucleic acid constructs increase the anti-Aβ titers in non-transgenic and Tg2576 mice. The increase in anti-Aβ titers is significantly greater in non-transgenic mice compared to the Tg2576 mice, indicating that Tg2576 mice do not respond as well to Aβ as an immunogen as do their non-transgenic littermates. These data show that pAG3BRI-Aβ expression plasmids can be used as DNA vaccines for generating an immune response toward Aβ.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A construct comprising a first nucleic acid molecule joined at its 3' end to nucleotides comprising a multiple cloning site, wherein said first nucleic acid molecule encodes an amino terminal region of a BRI polypeptide, wherein said amino terminal region of a BRI polypeptide has at least 95% sequence identity to residues 1-243 of SEQ ID NO:2 and consists essentially of a transmembrane signal sequence, a transmembrane spanning domain and a proprotein convertase (PC) cleavage sequence.

2. A construct comprising a first nucleic acid molecule operably linked at its 3' end to a second nucleic acid molecule, wherein said first nucleic acid molecule encodes an amino terminal region of a BRI polypeptide, and wherein said second nucleic acid molecule encodes a heterologous polypeptide, wherein said amino terminal region of a BRI polypeptide has at least 95% sequence identity to residues 1-243 of SEQ ID NO:2 and consists essentially of a transmembrane signal sequence, a transmembrane spanning domain and a proprotein convertase (PC) cleavage sequence.

3. The construct of claim 2, wherein said heterologous polypeptide is a β-amyloid polypeptide.

4. The construct of claim 2, wherein said operable linkage comprises nucleotides encoding a dibasic cleavage site.

5. The construct of claim 4, wherein said dibasic cleavage site comprises Lysine-Arginine.

6. The construct of claim 2, further comprising a promoter operably linked to the 5' end of said first nucleic acid molecule.

7. The construct of claim 6, wherein said promoter is a prion promoter.

8. The construct of claim 7, wherein said prion promoter is a mouse prion promoter.

9. The construct of claim 6, wherein said promoter is a β-actin promoter.

10. The construct of claim 9, wherein said β-actin promoter is a chicken β-actin promoter.

11. The construct of claim 1, wherein said BRI polypeptide is a human BRI polypeptide.

12. The construct of claim 1, wherein said BRI polypeptide is a mouse BRI polypeptide.

13. The construct of claim 3, wherein said β-amyloid polypeptide is selected from the group consisting of a wild-type β-amyloid polypeptide, a naturally occurring mutant of a β-amyloid polypeptide, a truncated amyloid β-polypeptide, and a β amyloid polypeptide containing substitutions at one or more residues.

14. The construct of claim 3, wherein said β-amyloid polypeptide is a mammalian β-amyloid polypeptide.

15. The construct of claim 14, wherein said mammalian β-amyloid polypeptide is selected from the group consisting of a human, a mouse, a guinea pig, and a rat β-amyloid polypeptide.

16. An isolated nucleic acid molecule consisting essentially of nucleotides encoding an amino terminal region of a BRI polypeptide, wherein said amino terminal region of a BRI polypeptide has at least 95% sequence identity to residues 1-243 of SEQ ID NO:2 and consists essentially of a transmembrane signal sequence, a transmembrane spanning domain and a proprotein convertase (PC) cleavage sequence.

17. The construct of claim 1, wherein said amino terminal region of a BRI polypeptide consists essentially of residues 1-243 of SEQ ID NO:2.

18. The construct of claim 2, wherein said amino terminal region of a BRI polypeptide consists essentially of residues 1-243 of SEQ ID NO:2.

19. A construct comprising a first nucleic acid molecule joined at its 3' end to nucleotides comprising a multiple cloning site, wherein said first nucleic acid molecule encodes an amino terminal region of a BRI polypeptide, wherein said amino terminal region of a BRI polypeptide consists essentially of a transmembrane signal sequence, a transmembrane spanning domain and a proprotein convertase (PC) cleavage sequence, wherein said first nucleic acid molecule consists essentially of nucleotides 1-729 of SEQ ID NO:1 and hybridizes under high stringency conditions to a fragment of at least 20 nucleotides from nucleotides 1-729 of SEQ ID NO:1.

20. A construct comprising a first nucleic acid molecule operably linked at its 3' end to a second nucleic acid molecule, wherein said first nucleic acid molecule encodes an amino terminal region of a BRI polypeptide, and wherein said second nucleic acid molecule encodes a heterologous polypeptide, wherein said amino terminal region of a BRI polypeptide consists essentially of a transmembrane signal sequence, a transmembrane spanning domain and a proprotein convertase (PC) cleavage sequence, wherein said first nucleic acid molecule consists essentially of nucleotides 1-729 of SEQ ID NO:1 and hybridizes under high stringency conditions to a fragment of at least 20 nucleotides from nucleotides 1-729 of SEQ ID NO:1.

21. The construct of claim 20, wherein said operable linkage comprises nucleotides encoding a dibasic cleavage site.

22. The construct of claim 21, wherein said dibasic cleavage site comprises Lysine-Arginine.

23. The construct of claim 20, further comprising a promoter operably linked to the 5' end of said first nucleic acid molecule.

24. The construct of claim 19, wherein said first nucleic acid is a human nucleic acid.

25. The construct of claim 20, wherein said first nucleic acid is a human nucleic acid.

* * * * *

SEQUENCE LISTING

<160> NUMBER OF SEQ ID NOS: 12

<210> SEQ ID NO 1
<211> LENGTH: 852
<212> TYPE: DNA
<213> ORGANISM: Artificial Sequence
<220> FEATURE:
<223> OTHER INFORMATION: Recombinant construct containing nucleic acid
      sequences encoding an amino terminal portion of human BRI operably linked to human Abeta1-40

<400> SEQUENCE: 1

```
atggtgaagg tgacgttcaa ctccgctctg gcccagaagg aggccaagaa ggacgagccc    60
aagagcggcg aggaggcgct catcatcccc cccgacgccg tcgcggtgga ctgcaaggac   120
ccagatgatg tggtaccagt tggccaaaga agagcctggt gttggtgcat gtgctttgga   180
ctagcattta tgcttgcagg tgttattcta ggaggagcat acttgtacaa atattttgca   240
cttcaaccag atgacgtgta ctactgtgga ataaagtaca tcaaagatga tgtcatctta   300
aatgagccct ctgcagatgc cccagctgct ctctaccaga caattgaaga aaatattaaa   360
atctttgaag aagaagaagt tgaatttatc agtgtgcctg tcccagagtt tgcagatagt   420
gatcctgcca acattgttca tgactttaac aagaaactta cagcctattt agatcttaac   480
ctggataagt gctatgtgat ccctctgaac acttccattg ttatgccacc cagaaaccta   540
ctggagttac ttattaacat caaggctgga acctatttgc ctcagtccta tctgattcat   600
gagcacatgg ttattactga tcgcattgaa acattgatcc cctgggtttt ctttatttat   660
cgactgtgtc atgacaagga aacttacaaa ctgcaacgca gagaaactat taaaggtatt   720
cagaaacgtg atgcagaatt ccgacatgac tcaggatatg aagttcatca tcaaaaattg   780
gtgttctttg cagaagatgt gggttcaaac aaaggtgcaa tcattggact catggtgggc   840
ggtgttgtct ag                                                        852
```

<210> SEQ ID NO 2
<211> LENGTH: 283
<212> TYPE: PRT
<213> ORGANISM: Artificial Sequence
<220> FEATURE:
<223> OTHER INFORMATION: Heterologous polypeptide comprising an amino
      terminal portion of human BRI and human Abeta1-40

<400> SEQUENCE: 2

```
Met Val Lys Val Thr Phe Asn Ser Ala Leu Ala Gln Lys Glu Ala Lys
 1               5                  10                  15

Lys Asp Glu Pro Lys Ser Gly Glu Glu Ala Leu Ile Ile Pro Pro Asp
            20                  25                  30

Ala Val Ala Val Asp Cys Lys Asp Pro Asp Asp Val Val Pro Val Gly
        35                  40                  45

Gln Arg Arg Ala Trp Cys Trp Cys Met Cys Phe Gly Leu Ala Phe Met
    50                  55                  60

Leu Ala Gly Val Ile Leu Gly Gly Ala Tyr Leu Tyr Lys Tyr Phe Ala
65                  70                  75                  80

Leu Gln Pro Asp Asp Val Tyr Tyr Cys Gly Ile Lys Tyr Ile Lys Asp
                85                  90                  95

Asp Val Ile Leu Asn Glu Pro Ser Ala Asp Ala Pro Ala Ala Leu Tyr
           100                 105                 110

Gln Thr Ile Glu Glu Asn Ile Lys Ile Phe Glu Glu Glu Val Glu
       115                 120                 125

Phe Ile Ser Val Pro Val Pro Glu Phe Ala Asp Ser Asp Pro Ala Asn
   130                 135                 140

Ile Val His Asp Phe Asn Lys Lys Leu Thr Ala Tyr Leu Asp Leu Asn
145                 150                 155                 160

Leu Asp Lys Cys Tyr Val Ile Pro Leu Asn Thr Ser Ile Val Met Pro
               165                 170                 175

Pro Arg Asn Leu Leu Glu Leu Leu Ile Asn Ile Lys Ala Gly Thr Tyr
```

-continued

```
                 180             185             190
Leu Pro Gln Ser Tyr Leu Ile His Glu His Met Val Ile Thr Asp Arg
        195                 200                 205

Ile Glu Asn Ile Asp His Leu Gly Phe Phe Ile Tyr Arg Leu Cys His
    210                 215                 220

Asp Lys Glu Thr Tyr Lys Leu Gln Arg Arg Glu Thr Ile Lys Gly Ile
225                 230                 235                 240

Gln Lys Arg Asp Ala Glu Phe Arg His Asp Ser Gly Tyr Glu Val His
            245                 250                 255

His Gln Lys Leu Val Phe Phe Ala Glu Asp Val Gly Ser Asn Lys Gly
        260                 265                 270

Ala Ile Ile Gly Leu Met Val Gly Gly Val Val
        275                 280
```

<210> SEQ ID NO 3
<211> LENGTH: 858
<212> TYPE: DNA
<213> ORGANISM: Artificial Sequence
<220> FEATURE:
<223> OTHER INFORMATION: Recombinant construct containing nucleic acid
      sequences encoding an amino Terminal portion of human BRI operably
      linked to human Abeta1-42

<400> SEQUENCE: 3

```
atggtgaagg tgacgttcaa ctccgctctg gcccagaagg aggccaagaa ggacgagccc    60
aagagcggcg aggaggcgct catcatcccc cccgacgccg tcgcggtgga ctgcaaggac   120
ccagatgatg tggtaccagt tggccaaaga agagcctggt gttggtgcat gtgctttgga   180
ctagcattta tgcttgcagg tgttattcta ggagagcat acttgtacaa atattttgca    240
cttcaaccag atgacgtgta ctactgtgga ataaagtaca tcaaagatga tgtcatctta   300
aatgagccct ctgcagatgc cccagctgct ctctaccaga caattgaaga aaatattaaa   360
atctttgaag aagaagaagt tgaatttatc agtgtgcctg tcccagagtt tgcagatagt   420
gatcctgcca acattgttca tgactttaac aagaaactta cagcctattt agatcttaac   480
ctggataagt gctatgtgat ccctctgaac acttccattg ttatgccacc agaaacccta   540
ctggagttac ttattaacat caaggctgga acctatttgc ctcagtccta tctgattcat   600
gagcacatgg ttattactga tcgcattgaa acattgatc acctgggttt ctttatttat    660
cgactgtgtc atgacaagga aacttacaaa ctgcaacgca gagaaactat taaaggtatt   720
cagaaacgtg atgcagaatt ccgacatgac tcaggatatg aagttcatca tcaaaaattg   780
gtgttctttg cagaagatgt gggttcaaac aaaggtgcaa tcattggact catggtgggc   840
ggtgttgtca tagcgtag                                                 858
```

<210> SEQ ID NO 4
<211> LENGTH: 285
<212> TYPE: PRT
<213> ORGANISM: Artificial Sequence
<220> FEATURE:
<223> OTHER INFORMATION: Heterologous polypeptide comprising an amino
      terminal portion of human BRI and human Abeta1-42

<400> SEQUENCE: 4

```
Met Val Lys Val Thr Phe Asn Ser Ala Leu Ala Gln Lys Glu Ala Lys
  1               5                  10                  15

Lys Asp Glu Pro Lys Ser Gly Glu Glu Ala Leu Ile Ile Pro Pro Asp
             20                  25                  30
```

```
Ala Val Ala Val Asp Cys Lys Asp Pro Asp Val Val Pro Val Gly
        35                  40                  45

Gln Arg Arg Ala Trp Cys Trp Cys Met Cys Phe Gly Leu Ala Phe Met
 50                  55                  60

Leu Ala Gly Val Ile Leu Gly Gly Ala Tyr Leu Tyr Lys Tyr Phe Ala
 65                  70                  75                  80

Leu Gln Pro Asp Asp Val Tyr Tyr Cys Gly Ile Lys Tyr Ile Lys Asp
                 85                  90                  95

Asp Val Ile Leu Asn Glu Pro Ser Ala Asp Ala Pro Ala Ala Leu Tyr
             100                 105                 110

Gln Thr Ile Glu Glu Asn Ile Lys Ile Phe Glu Glu Glu Val Glu
             115                 120                 125

Phe Ile Ser Val Pro Val Pro Glu Phe Ala Asp Ser Asp Pro Ala Asn
         130                 135                 140

Ile Val His Asp Phe Asn Lys Lys Leu Thr Ala Tyr Leu Asp Leu Asn
145                 150                 155                 160

Leu Asp Lys Cys Tyr Val Ile Pro Leu Asn Thr Ser Ile Val Met Pro
                165                 170                 175

Pro Arg Asn Leu Leu Glu Leu Leu Ile Asn Ile Lys Ala Gly Thr Tyr
            180                 185                 190

Leu Pro Gln Ser Tyr Leu Ile His Glu His Met Val Ile Thr Asp Arg
        195                 200                 205

Ile Glu Asn Ile Asp His Leu Gly Phe Phe Ile Tyr Arg Leu Cys His
    210                 215                 220

Asp Lys Glu Thr Tyr Lys Leu Gln Arg Arg Glu Thr Ile Lys Gly Ile
225                 230                 235                 240

Gln Lys Arg Asp Ala Glu Phe Arg His Asp Ser Gly Tyr Glu Val His
                245                 250                 255

His Gln Lys Leu Val Phe Phe Ala Glu Asp Val Gly Ser Asn Lys Gly
            260                 265                 270

Ala Ile Ile Gly Leu Met Val Gly Gly Val Val Ile Ala
        275                 280                 285

<210> SEQ ID NO 5
<211> LENGTH: 27
<212> TYPE: DNA
<213> ORGANISM: Artificial Sequence
<220> FEATURE:
<223> OTHER INFORMATION: Oligonucleotide

<400> SEQUENCE: 5
ttccctcgag tctcagccgc ccggagc                                    27

<210> SEQ ID NO 6
<211> LENGTH: 30
<212> TYPE: DNA
<213> ORGANISM: Artificial Sequence
<220> FEATURE:
<223> OTHER INFORMATION: Oligonucleotide

<400> SEQUENCE: 6
actgctcgag atgtaaaggg tggggttatg                                 30

<210> SEQ ID NO 7
<211> LENGTH: 39
<212> TYPE: DNA
<213> ORGANISM: Artificial Sequence
<220> FEATURE:
<223> OTHER INFORMATION: Oligonucleotide
```

```
<400> SEQUENCE: 7 attttttaagc ttctcgagag gctgcaatcg cagcgggag                          39

<210> SEQ ID NO 8
<211> LENGTH: 43
<212> TYPE: DNA
<213> ORGANISM: Artificial Sequence
<220> FEATURE:
<223> OTHER INFORMATION: Oligonucleotide

<400> SEQUENCE: 8
gtcggaattc tgcatcacgt ttctgaatac ctttaatagt ttc                      43

<210> SEQ ID NO 9
<211> LENGTH: 32
<212> TYPE: DNA
<213> ORGANISM: Artificial Sequence
<220> FEATURE:
<223> OTHER INFORMATION: Oligonucleotide

<400> SEQUENCE: 9
tggagatctg atgcagaatt ccgacatgac tc                                  32

<210> SEQ ID NO 10
<211> LENGTH: 35
<212> TYPE: DNA
<213> ORGANISM: Artificial Sequence
<220> FEATURE:
<223> OTHER INFORMATION: Oligonucleotide

<400> SEQUENCE: 10
taaaaggatc cctagacaac accgcccacc atgag                               35

<210> SEQ ID NO 11
<211> LENGTH: 41
<212> TYPE: DNA
<213> ORGANISM: Artificial Sequence
<220> FEATURE:
<223> OTHER INFORMATION: Oligonucleotide

<400> SEQUENCE: 11
taaaaggatc cctacgctat gacaacaccg cccaccatga g                        41

<210> SEQ ID NO 12
<211> LENGTH: 10
<212> TYPE: DNA
<213> ORGANISM: Homo sapien

<400> SEQUENCE: 12
tttaatttgt                                                           10
```